US009587248B2

(12) United States Patent
Trick et al.

(10) Patent No.: US 9,587,248 B2
(45) Date of Patent: Mar. 7, 2017

(54) MAYETIOLA DESTRUCTOR SUSCEPTIBILITY GENE ONE (MDS-1) AND ITS APPLICATION IN PEST MANAGEMENT

(75) Inventors: Harold Trick, Olsburg, KS (US); Xiuming Liu, Manhattan, KS (US); Ming-Shun Chen, Manhattan, KS (US)

(73) Assignees: THE UNITED STATES OF AMERICA AS REPRESENTED BY THE SECRETARY OF AGRICULTURE, Washington, DC (US); KANSAS STATE UNIVERSITY RESEARCH FOUNDATION, Manhattan, KS (US)

( * ) Notice: Subject to any disclaimer, the term of this patent is extended or adjusted under 35 U.S.C. 154(b) by 721 days.

(21) Appl. No.: 13/979,408

(22) PCT Filed: Jan. 9, 2012

(86) PCT No.: PCT/US2012/020631
§ 371 (c)(1),
(2), (4) Date: Jul. 12, 2013

(87) PCT Pub. No.: WO2012/096881
PCT Pub. Date: Jul. 19, 2012

(65) Prior Publication Data
US 2014/0026252 A1    Jan. 23, 2014

Related U.S. Application Data

(60) Provisional application No. 61/432,038, filed on Jan. 12, 2011.

(51) Int. Cl.
*C12N 15/82* (2006.01)
*C07K 14/415* (2006.01)

(52) U.S. Cl.
CPC ........ *C12N 15/8286* (2013.01); *C07K 14/415* (2013.01); *C12N 15/8279* (2013.01)

(58) Field of Classification Search
CPC .................................................. C12N 15/8279
See application file for complete search history.

(56) References Cited

U.S. PATENT DOCUMENTS 7,214,786 B2    5/2007 Kovalic et al.
2002/0053097 A1*    5/2002 Lindquist ............. C07K 14/415
800/298

(Continued)

FOREIGN PATENT DOCUMENTS

EP        2100962        9/2009
WO        9958659        11/1999
WO        2010006804     1/2010

OTHER PUBLICATIONS

Kim, Nak Hyun, and Byung Kook Hwang. "Pepper heat shock protein 70a interacts with the type III effector AvrBst and triggers plant cell death and immunity." Plant physiology (2014): pp. 114.*

(Continued)

*Primary Examiner* — Amjad Abraham
*Assistant Examiner* — Fan Weihua
(74) *Attorney, Agent, or Firm* — Hovey Williams LLP

(57) ABSTRACT

Plants having increased resistance to a pest relative to corresponding control plants are provided. The resistant plants have inhibited expression, activity, or function of a susceptibility gene, and thereby have decreased expression, activity, or function of the susceptibility gene in the presence of the pest as compared to a control plant in which the wild-type susceptibility gene is normally expressed in the presence of the pest. Methods of producing plants with increased resistance are also provided. The methods involve altering the expression, activity, or function of a susceptibility gene, such as Mds-1, in the plant. Isolated Mds-1

(Continued)

sequences are provided that can be manipulated to enhance pest resistance in modified plants. Modified plants, plant cells, tissues, seeds, and progeny are also provided having enhanced pest resistance.

12 Claims, 10 Drawing Sheets

(56) References Cited

U.S. PATENT DOCUMENTS

| | | | |
|---|---|---|---|
| 2008/0244788 A1* | 10/2008 | Matchett | A01H 5/10 800/269 |
| 2009/0165173 A1 | 6/2009 | Kogel et al. | |
| 2009/0222942 A1 | 9/2009 | Wagner et al. | |

OTHER PUBLICATIONS

Sung, Dong Yul, and Charles L. Guy. "Physiological and molecular assessment of altered expression of Hsc70-1 in Arabidopsis. Evidence for pleiotropic consequences." Plant Physiology 132.2 (2003): 979-987.*

Lu, Rui, et al. "High throughput virus-induced gene silencing implicates heat shock protein 90 in plant disease resistance." The EMBO Journal 22.21 (2003): 5690-5699.*

Van Ooijen, Gerben, et al. "The small heat shock protein 20 RSI2 interacts with and is required for stability and function of tomato resistance protein I-2." The Plant Journal 63.4 (2010): 563-572.*

Zeiss, M. R., R. L. Brandenburg, and J. W. Van Duyn. "Suitability of seven grass weeds as Hessian fly (Diptera: Cecidomyiidae) hosts." J. Agric. Entomol 10.2 (1993): 107-119.*

Luo, Zhenghua, and Zhixiang Chen. "Improperly terminated, unpolyadenylated mRNA of sense transgenes is targeted by RDR6-mediated RNA silencing in Arabidopsis." The Plant Cell 19.3 (2007): 943-958.*

Duster, published by Oklahoma Foundation Seed Stocks, and updated on Apr. 1, 2010, retrieved online from www.ofssinc.com.*

Liu, Xuming, et al. "Wheat Mds-1 encodes a heat-shock protein and governs susceptibility towards the Hessian fly gall midge." Nature communications 4 (2013).*

Bryan, G. J., et al. "Low levels of DNA sequence variation among adapted genotypes of hexaploid wheat." Theoretical and Applied Genetics 99.1-2 (1999): 192-198.*

Pavan, Stefano, et al. "Loss of susceptibility as a novel breeding strategy for durable and broad-spectrum resistance." Molecular Breeding 25.1 (2010): 1-12.*

Yang, Bing, Akiko Sugio, and Frank F. White. "Os8N3 is a host disease-susceptibility gene for bacterial blight of rice." Proceedings of the National Academy of Sciences 103.27 (2006): 10503-10.*

Waters, E. R. "The molecular evolution of the small heat-shock proteins in plants." Genetics 141.2 (1995): 785-795.*

McElwain, Elizabeth, "A Wheat cDNA Clone Which is Homologous to the 17kd Heat-shock Protein Gene Family of Soybean," Nucleic Acids Research, 1989, vol. 17, No. 4.

Liu, Xuming, "Gene Expression of Different Wheat Genotypes During Attack by Virulent and Avirulent Hessian Fly (*Mayetiola destructor*) Larvae," J. Chem. Ecol., 2171-2194, vol. 33; Nov. 16, 2007.

Wu, Junxiang, "Differential Responses of Wheat Inhibitor-like Genes to Hessian Fly, *Mayetiola destructor*, Attacks During Compatible and Incompatible Interactions," J. Chem Ecol, 2008, 1005-1012, vol. 34; Jun. 27, 2008.

The International Search Report and Written Opinion dated Aug. 28, 2012 in corresponding PCT/US2012/020631 filed on Jan. 9, 2009.

* cited by examiner

MAYETIOLA DESTRUCTOR SUSCEPTIBILITY GENE ONE (MDS-1) AND ITS APPLICATION IN PEST MANAGEMENT

CROSS-REFERENCE TO RELATED APPLICATIONS

The present application is the National Stage of International Application No. PCT/US2012/020631, filed Jan. 9, 2012, which claims the priority benefit of U.S. Provisional Patent Application Ser. No. 61/432,038, filed Jan. 12, 2011, entitled *MAYETIOLA DESTRUCTOR* SUSCEPTIBILITY GENE ONE (MDS-1) AND ITS APPLICATION IN PEST MANAGEMENT, each of which is incorporated by reference in its entirety herein.

FEDERALLY SPONSORED RESEARCH OR DEVELOPMENT

This invention was made with government support under contract number 2009-35302-05262 awarded by the United States Department of Agriculture. The United States government has certain rights in the invention.

SEQUENCE LISTING

The following application contains a sequence listing in computer readable format (CRF), submitted as a text file in ASCII format entitled "Sequence_Listing," created on Jan. 5, 2012, as 12 KB. The content of the CRF is hereby incorporated by reference.

BACKGROUND OF THE INVENTION

Field of the Invention

The present invention relates to plants having increased resistance to pests through alteration of plant susceptibility genes and methods of producing the same.

Description of Related Art

Many parasitic insects and microbes attack plants by suppressing plant defenses and inducing other changes to the benefit of the pest. Often, the manipulation of plants by parasites is a necessary prerequisite for host susceptibility. *Mayetiola destructor* (MD, the Hessian fly), a destructive insect pest of wheat, is one example of these types of parasitic insects. The Hessian fly is a gall midge, and galling insects, such as the Hessian fly, manipulate host plants to induce the formation of galls (nutritive cells) for the benefit of the insect, as well as alter plant metabolism. The Hessian fly, in particular, manipulates host plants extensively. A single Hessian fly larva (less than 1 μm long) can irreversibly inhibit wheat growth, induce the formation of nutritive tissue at the feeding site, and reprogram metabolic pathways of susceptible host plants. As a result, an infested plant becomes stunted, and the whole plant acts like a gall with the insect feeding site as the nutrient sink. If plant manipulation and thus the formation of galls is prevented, galling insects cannot survive and plants become resistant to attack. Previously, the Hessian fly and other parasitic pests have been controlled by developing cultivars with resistance mediated by major resistance (R) genes that have a typical gene-for-gene interaction with pest avirulence. According to the general gene-for-gene theory of resistance, a successful resistance is triggered only if a resistance gene product in the plant recognizes a specific avirulence gene product from the pest. This effector-triggered immunity in plants is widely employed as a cost-effective and environmentally-friendly measure for pest management. The major challenge for this resistance gene approach is that the period of effective resistance mediated by R genes is short, lasting only about 6-8 years. This short-lived resistance is a major hindrance for wide adaptation of cultivars with resistance to multiple pests.

In addition, compatible and incompatible interactions can be temperature sensitive. That is, susceptibility can reoccur, even in plants containing R genes, if the plants are shifted to a temperature exceeding their normal growth temperature by a certain number of degrees. For wheat, this temperature is approximately 10° C. higher than their normal growth temperature of about 20° C. Thus, the effect of the R genes can be neutralized by high temperature, which suggests a relationship between plant resistance and susceptibility as follows. In particular, one or more targets exist in the plant essential for susceptibility manipulation by the pest. When these targets are activated, through either increased expression or other means during compatible interactions, plants can be successfully manipulated by the pest and become susceptible. When the activation of these targets is prevented through an R gene effect, plants cannot be manipulated by the pest and therefore are resistant. The targets can also be activated in plants under high temperature independent of the R gene effect, and the activation of the targets is sufficient for the pests to manipulate plants, resulting in plant susceptibility even in the presence of an R gene. Most, if not all, Hessian fly resistance genes identified in wheat are temperature sensitive, and resistance is lost when the plants are exposed to high temperature (30-37° C.) for a given period of time.

Thus, there remains a need in the art for improved methods of increasing plant resistance to pests, even under elevated temperature conditions.

SUMMARY OF THE INVENTION

Instead of focusing on resistance genes, as in the prior art, the present invention provides a new strategy for pest management based on knocking down the expression of susceptibility genes. Because the susceptibility pathway is likely common to different biotypes of parasitic pests, resistance mediated by susceptibility gene-knockdown should be more durable than the resistance gene approach, and therefore, more economical and effective. The invention also provides technology wherein knockdown of a gene can provide resistance to multiple pests, whereas current resistance genes only provide resistance to specific species or biotypes. In one aspect, the invention provides a plant having increased resistance to a pest relative to a control plant, wherein the control plant comprises a wild-type (endogenous) susceptibility gene that is normally expressed in the presence of the pest. In contrast, the resistant plant comprises a corresponding susceptibility gene, the expression, activity, or function of which is inhibited in the resistant plant.

A method of producing a resistant plant having increased resistance to a pest relative to a corresponding control plant is also provided, wherein the control plant comprises a wild-type susceptibility gene that is normally expressed in the presence of the pest. The method comprises inhibiting the expression, activity, or function of a susceptibility gene in a plant to thereby produce the resistant plant. Advantageously, the expression, activity, or function of the susceptibility gene in the resistant plant is inhibited in the presence of the pest thereby conferring to the plant resistance to the pest.

A method for producing a plant having increased resistance to *Mayetiola destructor* relative to a corresponding control plant is also provided, wherein the control plant comprises a wild-type susceptibility gene that is normally expressed in the presence of *Mayetiola destructor*. The method comprises: (a) culturing immature plant embryos to form callus tissue; (b) inhibiting expression or activity of the susceptibility gene in the tissue to produce modified plant cells; and (c) regenerating resistant plants from the modified plant cells, wherein the expression, activity, or function of the susceptibility gene in the resistant plants is inhibited in the presence of *Mayetiola destructor*.

The invention also provides a transgenic plant comprising a nucleotide sequence that encodes and/or is complementary to a sequence that encodes a Mds-1 polynucleotide sequence of SEQ ID NO:4 or an antisense sequence of SEQ ID NO:4. Advantageously, the transgenic plant has increased resistance to *Mayetiola destructor*.

A nucleic acid construct is also provided. The construct comprises a nucleotide sequence or antisense sequence of SEQ ID NO:4 operably linked to a promoter that drives expression in a plant cell. The invention also provides a vector comprising this nucleic acid construct, as well as a transgenic plant having this nucleic acid construct stably incorporated in its genome.

A further method of generating or increasing resistance to at least one pest in a plant is also provided. The plant comprises a susceptibility gene that is normally expressed in the presence of the pest. The method comprises inhibiting expression, activity, or function of the susceptibility gene in the plant, or a tissue, organ, part, or cell thereof, wherein the inhibiting comprises introducing into the plant, tissue, organ, part, or cell thereof a nucleic acid encoding a double-stranded RNA that inhibits expression, activity, or function of the susceptibility gene.

An isolated nucleic acid comprising a nucleic acid sequence encoding a wheat Mds-1 protein comprising SEQ ID NO:3 or the functional equivalent thereof is also provided. The invention also provides a further isolated nucleic acid comprising the sequence of SEQ ID NO: 1, the complement thereof, or conservatively modified variants thereof. The invention is also concerned with a vector comprising a nucleic acid construct comprising SEQ ID NO:4, as well as a transgenic plant comprising this vector.

The invention also provides a recombinant plant cell. More specifically, the expression, activity, or function of an endogenous Mds-1 protein in the plant cell is reduced by stable transformation with a nucleic acid as compared to an untransformed plant cell, wherein the nucleic acid encodes a double-stranded RNA that inhibits the expression, activity, or function of a susceptibility gene encoding for the Mds-1 protein.

In a further aspect of the invention, another method for increasing pest resistance in a plant, is provided. The method comprises inhibiting the expression, activity, or function of a plant susceptibility gene Mds-1, wherein the gene comprises a sequence selected from the group consisting of: (a) a nucleotide sequence comprising SEQ ID NO:2; (b) a nucleotide sequence comprising an antisense sequence corresponding (e.g., complementary) to SEQ ID NO:2; (c) a nucleotide sequence having at least about 50% sequence identity to SEQ ID NO:1; (d) a nucleotide sequence encoding an Mds-1 protein comprising SEQ ID NO:3; and (e) a nucleotide sequence encoding an protein having at least about 30% amino acid identity to SEQ ID NO:3 and retaining the functional characteristics thereof.

The invention also provides a further transgenic plant having decreased expression, activity, or function of a plant susceptibility gene Mds-1, wherein the plant has stably incorporated into its genome a DNA construct. The DNA construct comprises at least one nucleotide sequence selected from the group consisting of: (a) a nucleotide sequence comprising SEQ ID NO:4; (b) a nucleotide sequence comprising an antisense sequence corresponding to SEQ ID NO:4; (c) a nucleotide sequence having at least about 50% sequence identity to SEQ ID NO:4; (d) a nucleotide sequence encoding an Mds-1 protein comprising SEQ ID NO:3; and (e) a nucleotide sequence encoding an Mds-1 protein having at least about 30% amino acid identity to SEQ ID NO:3 and retaining the functional characteristics thereof, wherein the nucleotide sequence is operably linked to a promoter capable of regulating transcription of the sequence in the plant.

A further isolated nucleotide sequence is also provided in the invention. The sequence comprises at least one of the nucleotide sequences selected from the group consisting of: (a) a nucleotide sequence comprising SEQ ID NO:2; (b) a nucleotide sequence comprising an antisense sequence corresponding to SEQ ID NO:2; (c) a nucleotide sequence having at least about 50% sequence identity to SEQ ID NO:1; (d) a nucleotide sequence encoding an Mds-1 protein comprising SEQ ID NO:3; and (e) a nucleotide sequence encoding an Mds-1 protein having at least about 30% amino acid identity to SEQ ID NO:3 and retaining the functional characteristics thereof.

The invention is also concerned with additional methods for increasing or enhancing resistance to a pest in a plant. The methods comprise providing a first parent plant comprising a susceptibility gene that is normally expressed in the presence of the pest, wherein the expression, activity, or function of the susceptibility gene is inhibited in the first parent plant. The first parent plant is crossed with a second parent plant to produce progeny plants, and then progeny plants having inhibited expression, activity, or function of the susceptibility gene are selected. Advantageously, the progeny plants, like the first parent plant, also have increased or enhanced resistance to the pest.

Thus, through the various methods, techniques, and nucleic acid sequences disclosed herein, the present invention broadly provides wheat cultivars with Mds-1-knockdown or Mds-1 mutants that are resistant to Hessian fly and other sucking mouthpart insects including orange blossom midge and various aphids. The invention also provides methods of producing barley cultivars with Mds-1-knockdown or Mds-1 mutants that are resistant to Hessian fly, Barley stem gall midge, and other sucking mouthpart insects, as well as rice cultivars with Mds-1-knockdown or Mds-1 mutants that are resistant to Asian rice midge, brown plant hopper, and other sucking mouthpart insects. The invention also provides techniques for increasing resistance in other crop plants with Mds-1-knockdown or Mds-1 mutants to sucking mouthpart insects, including the production of vegetables that are resistant to white flies. Additional advantages of the invention will become apparent from the following description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
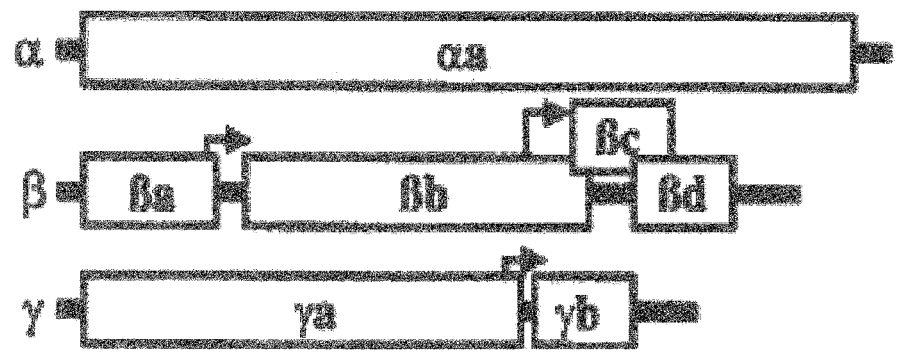
FIG. 1A is a schematic representation of the barley stripe mosaic virus (BSMV) genome consisting of 3 subgenomes (tripartite α, β, and γ) used for VIGS in Example 5.

In more detail, the present invention is concerned with plants having inhibited expression, activity, or function of a target susceptibility gene, which thereby have increased resistance to pest manipulation and infestation relative to corresponding control plants in which the wild-type (or endogenous) susceptibility gene is normally expressed in the presence of the pest (e.g., during a compatible interaction). Such plants are referred to herein as "resistant" plants. The invention is also concerned with various methods of increasing resistance to a pest by knocking down a target susceptibility gene in a plant, or a tissue, organ, part, or cell thereof. In some embodiments, the susceptibility gene encodes for a heat shock protein. Advantageously, plants produced according to the present invention, unlike previous cultivars, maintain resistance to a given pest even under elevated temperatures (e.g., temperatures at least about 10° C. higher than normal plant growing temperatures). For wheat, "elevated growing temperatures" are considered to be temperatures greater than about 25° C., preferably greater than about 27° C., and more preferably greater than about 30° C.

The inventive methods can be applied to increase resistance in monocotyledonous as well as dicotyledonous plants. Examples of preferred monocotyledonous plants for use in the invention include wheat (*Triticum* sp.), barley (*Hordeum* sp.), rice (*Oryza* sp.), maize (*Zea* sp.), rye (*Secale* sp.), and sorghum (sorghum bicolor). Examples of preferred dicotyledonous plants for use in the invention include soybeans (*Glycine* sp.), tomato (*Solanum* sp.), and cotton (*Gossypium* sp.). The method of the invention can be used to increase plant resistance to a wide variety of pests, including insects (particularly phytophagous insects and/or insects having sucking mouthparts) as well as other parasites and pathogens (particularly biotrophic pathogens), and disease. More specifically, the inventive methods can be used to produce plants having increased resistance to pests such as galling insects, other sucking mouthpart insects, parasitic nematodes, fungal pathogens, bacterial pathogens, and other plant manipulator pests. Specific examples of pests are selected from the group consisting of Hessian flies (*Mayetiola destructor*), Barley stem gall midges (*Mayetiola hordei*), Asian rice midges (*Orseolia oryzae*), orange blossom midges (*Sitodiplosis mosellana*), aphids, brown plant hopper (*Nilaparvata lugens*), white flies, lesion nematodes (*Pratylenchus neglectus* and *P. thornei*), cyst nematodes (*Heterodera glycines*), root knot nematodes (*Meloidogyne javanica* and *M. incognita*), burrowing nematodes (*Radopholus similis* and *Rotylenchulus reniformis*), powdery mildews, stem rust (*Ruccinia graminis*), leaf rust and stripe rust (*Puccinia* sp.), rice and wheat blast (*Magnaporthe grisea*), and combinations thereof. Thus, the term "pest" is used herein to encompass both insects (particularly phytophagous insects), as well as parasites, pathogens (particularly biotrophic pathogens), and other disease-causing agents, as described above.

According to a particularly preferred aspect of the invention, a wheat gene that is a target for manipulation by Hessian fly larva, named *Mayetiola destructor* susceptibility gene one (Mds-1), is inhibited. This gene is normally not expressed in the tissue of uninfested wheat plants, but is induced to high levels of expression in susceptible wheat following Hessian fly attack. The full gene is provided in SEQ ID NO:1, while the coding region is provided in SEQ ID NO:2. The Mds-1 protein sequence is provided in SEQ ID NO:3. Thus, according to a preferred aspect, the invention provides plants with increased resistance to these and other pests, preferably due to inhibited expression, activity, or function of the Mds-1 gene, a portion thereof, or a functional equivalent thereof. "Functional equivalents," as used herein, include sequences derived from or having at least about 50% sequence identity (preferably at least about 80% sequence identity, and more preferably at least about 90% sequence identity) to SEQ ID NO:1 or the coding region of Mds-1 (SEQ ID NO:2), and which encode the wild-type protein (SEQ ID NO:3), an amino acid sequence comprising at least about 30% amino acid identity (preferably at least about 50% amino acid identity, and more preferably at least about 80% amino acid identity) with SEQ ID NO:3, or which encode a protein having essentially the same functional characteristics thereof (i.e., conferring resistance when down regulated). More preferably, the invention provides a resistant plant which does not express Mds-1 wild-type protein (SEQ ID NO:3) or an amino acid sequence comprising at least about 30% amino acid identity (preferably at least about 50% amino acid identity, and more preferably at least about 80% amino acid identity) with SEQ ID NO:3 in the presence of the pest. According to a further aspect of the invention, resistance to a pest in a plant is increased by inhibiting the expression, function, or activity of a susceptibility gene which comprises a sequence selected from the group consisting of: (a) a nucleotide sequence comprising SEQ ID NO:2; (b) a nucleotide sequence comprising an antisense sequence corresponding to SEQ ID NO:2; (c) a nucleotide sequence having at least about 50% sequence identity (preferably at least about 80% sequence identity, and more preferably at least about 90% sequence identity) to SEQ ID NO:1 or SEQ ID NO:2 (i.e., conservatively modified variants thereof); (d) a nucleotide sequence encoding an Mds-1 protein comprising SEQ ID NO:3; and (e) a nucleotide sequence encoding an Mds-1 protein having at least about 30% amino acid identity (preferably at least about 50% amino acid identity, and more preferably at least about 80% amino acid identity) to SEQ ID NO:3 and retaining the functional characteristics thereof.

In general, the method of increasing resistance of a plant to a pest comprises inhibiting the expression, activity, or function of a target susceptibility gene in a plant cell to produce a modified cell. For example, the method can comprise culturing immature plant embryos to form callus tissue, followed by inhibiting the expression, activity, or function of the susceptibility gene in the tissue to produce modified plant cells (and in the case of transgenic techniques, transformed cells). The modified cells are then used to regenerate resistant plants having inhibited expression, activity, or function of the susceptibility gene, as described herein. Thus, in the resulting resistant plants the expression, activity, or function of the gene is reduced or diminished in the presence of a given pest as compared to the normal expression, activity, or function of the corresponding susceptibility gene in a control (i.e., non-modified) plant or cell.

The invention also provides resistant and/or transgenic cells, tissue, and seeds of plants produced by the methods described herein, and the progeny thereof.

It will be appreciated that the expression, activity, or function of a susceptibility gene in a plant can be inhibited by any suitable gene down-regulation technique, which can include modifying the target gene itself, as well as methods involving modification of adjacent sequences. For example, transgenic techniques can be used to alter expression of the target gene. In one aspect, the resistant plant can comprise a nucleic acid construct, preferably stably incorporated into its genome, which inhibits expression, activity, or function of the susceptibility gene. Thus, the resulting transgenic plant is prepared by introducing into a plant cell a nucleic acid construct that inhibits expression, activity, or function of the target susceptibility gene. More preferably, the nucleic acid encodes a double-stranded RNA that inhibits expression, activity, or function of the susceptibility gene. The nucleic acid construct can comprise a nucleotide sequence specific for the susceptibility gene which is operably linked to a promoter that drives expression in the plant cell. More preferably, the transgenic plant is prepared by introducing into a plant cell a vector comprising the nucleic acid construct. The construct or vector can be introduced by any suitable method, including, without limitation, a biolistic particle delivery system, microprojectile bombardment, viral infection, *Agrobacterium*-mediated transformation (*Agrobacterium tumelaciens*), electroporation, and liposomal delivery, to produce transformed cells. The term "bombardment" with respect to transformation refers to the process of accelerating particles towards a target biological sample (e.g., cell, tissue, etc.) to effect wounding of the cell membrane of a cell in the target biological sample and/or entry of the particles into the target biological sample.

In some embodiments, RNA interference (RNAi) is used to inhibit the expression, activity, or function of the target gene. More specifically, RNAi is used to reduce the expression of one or more transcripts normally induced during a compatible interaction between a pest and a corresponding infested host plant. RNAi relies on sequence-specific, post-transcriptional gene silencing, and is broadly defined herein to include all post-transcriptional and transcriptional mechanisms of RNA-mediated inhibition of gene expression. Generally, in RNAi, all or a portion of the target gene (typically greater than 200 bp) is duplicated in an expression vector in a sense/antisense or an antisense/sense orientation so that the resulting mRNA hybridizes to itself forming a large hairpin loop. This product in then processed by the cell into small interfering RNAs (siRNAs) which are approximately 21-24 nucleotides in length triggering RNAi and silencing the endogenous target gene. RNAi can be used to either partially or completely inhibit expression of the target gene. RNAi may also be considered to completely or partially inhibit the function of a target RNA. Thus, in one aspect, the nucleic acid construct preferably comprises a sense and/or an antisense sequence for the target susceptibility gene and encodes double stranded RNA that inhibits the expression, activity, or function of the target susceptibility gene. In a further aspect, the nucleic acid construct will preferably comprise a sense sequence operably linked to its complementary antisense sequence and encoding double stranded RNA that inhibits expression, activity, or function of the target susceptibility gene.

The nucleic acid construct can further comprise a selection gene, such as those selected from the group consisting of herbicide resistant genes (e.g., bar gene), antibiotic resistant genes, and other positively selectable genes. In this aspect, transformed cells are preferably grown on selection media corresponding to the desired selection gene to confirm transformation (i.e., incorporation of the construct). Transformation can also be confirmed by specific DNA detection (e.g., PCR) or other positive selection methods. Transgenic plants having inhibited expression, activity, or function of the target susceptibility gene are then regenerated from the transformed cells. The reduction in transcript level from gene silencing results in lowered levels of the target protein, resulting in phenotypic changes in the modified plant, cell, or tissue. According to a preferred aspect of the invention, the cells are transformed by delivering a selection gene and DNA coding for an antisense Mds-1 sequence into the cells of the callus tissue. Plants with *Mayetiola destructor* resistance are then developed and selected by growing transformed cells on media and selecting for the selection gene, wherein the resulting transgenic plant transcribes the Mds-1 sequence to form dsRNA, which inhibits the expression, activity, or function of the Mds-1 gene. Alternatively, the cells are transformed by delivering a selection gene and DNA coding for a sense Mds-1 sequence and antisense Mds-1 sequence into the cells of the callus tissue and selecting for *Mayetiola destructor* resistance as described above.

Virus-induced gene silencing (VIGS) can also be used to inhibit the expression, activity, or function of the target susceptibility gene. This technology uses plant viruses to express a small fragment of a host gene in the form of dsRNA in inoculated plants. The replication of the viral vector, which includes the target gene fragment, induces a host response that knocks down or inhibits expression of the endogenous target gene. The target sequence itself may be native or transgenic. In these embodiments, the plant is inoculated with a viral vector comprising a sequence (sense or antisense) of the targeted susceptibility gene, which encodes for RNA that inhibits the expression, activity, or function of the target gene to thereby produce the transgenic plant.

It will be appreciated that other known transgenic methods can also be utilized to silence the target gene, including microRNAs, artificial microRNAs, antisense RNA, or T-DNA insertional inactivation of the target gene or associated promoter. For example, in antisense gene silencing, DNA or RNA that is complementary to the mRNA of the target gene is introduced into a cell and inhibits translation of the gene product. This sequence can be all or a portion of the mRNA. Another approach to silence a gene is to use micro RNAs (miRNAs). miRNAs are another class of small RNAs which can cause specific gene silencing. The creation of artificial miRNAs in expression vectors is highly specific and only requires 19 to 21 nucleotides to be complementary to the endogenous gene target to induce gene silencing. In addition, gene knockouts that result in changes (mutations) in the target gene sequence itself or in the regulatory sequences within the associated promoter are also envisioned for use in the present invention to inhibit the expression, activity, or function of the target susceptibility gene.

Regardless of the transgenic technique, in one or more embodiments, the sense sequence used in the nucleic acid construct preferably comprises SEQ ID NO:4 or a sequence having at least about 50% sequence identity (preferably at least about 80% sequence identity, and more preferably at least about 90% sequence identity) with SEQ ID NO:4. Likewise, the antisense sequence preferably corresponds to SEQ ID NO:4 or a sequence having at least about 50% sequence identity (preferably at least about 80% sequence identity, and more preferably at least about 90% sequence identity) with SEQ ID NO:4. Thus, in one aspect of the invention there is provided a transgenic plant comprising a nucleotide sequence that encodes or is complementary to a sequence that encodes a Mds-1 polynucleotide sequence of SEQ ID NO:4, wherein the transgenic plant has increased resistance to *Mayetiola destructor*. In a further aspect of the invention, the nucleic acid construct comprises at least one nucleotide sequence selected from the group consisting of: (a) a nucleotide sequence comprising SEQ ID NO:4; (b) a nucleotide sequence comprising an antisense sequence corresponding to SEQ ID NO:4; (c) a nucleotide sequence having at least about 50% sequence identity (preferably at least about 80% sequence identity, and more preferably at least about 90% sequence identity) to SEQ ID NO:4; (d) a nucleotide sequence encoding an Mds-1 protein comprising SEQ ID NO:3; and (e) a nucleotide sequence encoding an Mds-1 protein having at least about 30% amino acid identity (preferably at least about 50% amino acid identity, and more preferably at least about 80% amino acid identity) to SEQ ID NO:3 and retaining the functional characteristics thereof. More preferably the nucleotide sequence is operably linked to a promoter capable of regulating transcription of the sequence in the transgenic plant. In a further embodiment, the nucleic acid construct could comprise any portion of SEQ ID NO:1 or SEQ ID NO:2 (similar to embodiments using SEQ ID NO:4 above), which could be used to inhibit the expression, activity, or function of the target susceptibility gene.

According to another aspect of the invention, the expression, activity, or function of the susceptibility gene in the resistant plant is inhibited by mutagenesis of the target susceptibility gene itself or of associated adjacent sequences affecting the expression, activity, or function of the target gene. Thus, the resistant plant preferably comprises an insertion, deletion, or point mutation which directly or indirectly inhibits the expression, activity, or function of the susceptibility gene. It will be appreciated that the mutation(s) can be induced by any suitable means, including chemically or with radiation according to known methods. Natural mutations which inhibit the expression, activity, or function of the target susceptibility gene or corresponding protein are also encompassed by the present invention.

Figure 15:
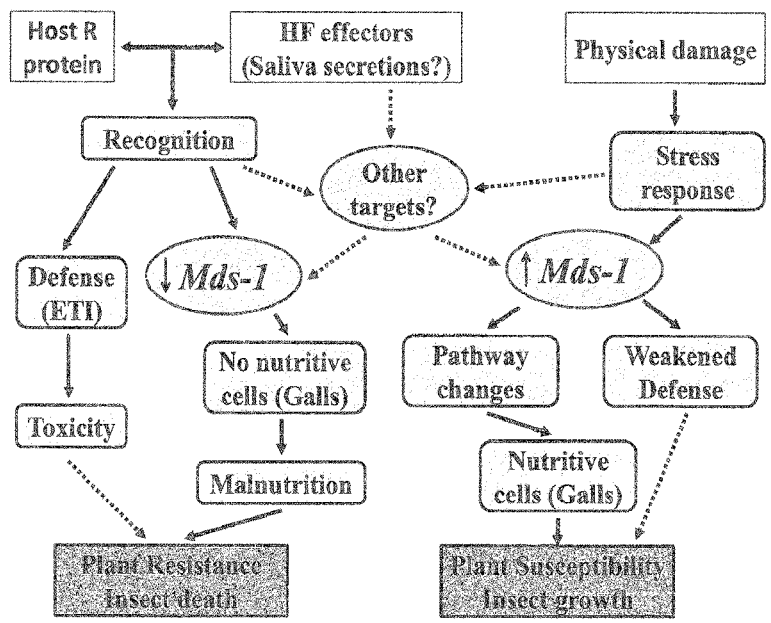
FIG. 15 is a model for Ws-1 involvement in plant susceptibility and resistance. Solid arrows between objects indicate effects based actual data, whereas dashed arrows indicate proposed effects, Arrows beside Mds-1 indicate down- or up-regulation, respectively.

It will also be appreciated that inhibition of the expression, activity, or function of Mds-1 can be based on conditional expression of Mds-1 driven by conditional promoters, according to known methods. Likewise, resistant cultivars can also be produced by interfering with other targets, such as gene products (e.g., proteins), in the Mds-1 pathway, which is depicted in FIG. 15.

Further, resistant plants can be produced indirectly by breeding parent plants having inhibited expression, activity, or function of the target susceptibility gene or corresponding gene products (whether naturally occurring or induced) with other resistant plants, or with other cultivars having additional desired characteristics (e.g., drought tolerance, geographic adaptation, stalk strength, etc.). The resulting progeny can then be screened to identify resistant progeny with inhibited expression, activity, or function of the corresponding target susceptibility gene or gene products.

Regardless of the embodiment, resistant plants according to the invention preferably exhibit a decrease in the expression of the susceptibility gene in the presence of the pest as compared to a corresponding control plant. More preferably, the plant has a decreased level of Mds-1 protein in the presence of the pest as compared to a corresponding control plant. Accordingly, the inventive plants have an increased or enhanced resistance to infestation or manipulation by the pest.

As used herein, the term "susceptibility gene" refers to a gene required for a compatible interaction between a pest and a corresponding host plant. That is, the gene is targeted for manipulation by the pest. A "compatible" interaction is defined as one in which the host plant is susceptible to infestation and disease and the pest is virulent, whereas an "incompatible" interaction is defined as one in which the pest is unable to develop disease or infestation in the host plant. The host plant in an incompatible interaction is resistant to the pest which is therefore referred to as being avirulent.

The phrase "in the presence of" is used herein to refer to the interaction of a host plant and a given pest, including manipulation (or attempted manipulation) of the plant by the pest.

The term "control" when used with respect to control plants includes wild-type (native) plants, as well as cultivars and genetically altered plants (such as plants containing resistance genes) that otherwise contain a wild-type, non-modified, or native (endogenous) susceptibility gene targeted for gene silencing (inhibition) according to the invention. A "wild-type" gene is one that has the characteristics of a gene isolated from a naturally occurring source. A "wild-type" gene product is one that has the characteristics of a gene product isolated from a naturally occurring source, whereas "modified" genes or gene products are those having modifications in sequence and/or functional properties (i.e., altered characteristics) when compared to the wild-type gene or gene product. Likewise, "modified" cells, tissues, seeds, etc. are those that have been altered to change the expression, activity, or function of the target genes or gene products, as opposed to non-modified cells, tissues, etc. Thus, the term "modified," as used herein, encompasses both transgenic and non-transgenic techniques (e.g., natural or induced mutagenesis).

The "inhibition," "silencing," or "knock down" of the expression, activity, or function of a gene, as used herein, is intended to refer to any suitable method of reducing or even completely suppressing protein expression from a gene or a coding sequence, including methods of reducing the levels of protein produced as a result of gene transcription to mRNA and subsequent translation of the mRNA. Gene inhibition may be effective against a native plant gene associated with a trait, e.g., to provide the plant with a diminished level of a protein encoded by the native gene or with reduced levels of an affected metabolite. Examples include RNAi, VIGS, and mutagenesis (including natural mutations), as described herein.

The term gene "expression" refers to the process of converting genetic information encoded in a gene into RNA (e.g., mRNA, rRNA, tRNA, or snRNA) through transcription of the gene (i.e., via the enzymatic action of an RNA polymerase), and into protein, through translation of mRNA. Gene expression can be regulated at many stages in the process. The term "overexpression" refers to the production of a gene product in transgenic plants that exceeds levels of production in normal, control, or non-transformed plants. References to altered "levels" of expression refers to the production of gene product(s) in modified plants, such as transgenic plants, in amounts or proportions that differ from that of normal, control, or non-modified plants.

The term "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced The term "vector" refers to nucleic acid molecules that transfer DNA segment(s) from one cell to another. The term includes recombinant DNA molecules containing a desired coding sequence(s) and appropriate nucleic acid sequences (e.g., promoters) necessary for the expression of the operably linked coding sequence in a particular host organism.

The term "transform" is used herein to refer to the introduction of foreign DNA into cells. Transformation may be accomplished by a variety of means known to the art and described herein.

The term "transgenic" is used herein to refer to a plant, a plant structure, a plant cell, a plant tissue, or a plant seed that contains at least one heterologous gene in one or more of its cells. The term "heterologous gene" refers to a gene encoding a factor that is not in its natural environment. For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

A "sense" strand of nucleic acid construct refers to a strand that is transcribed by a cell in its natural state into a "sense" mRNA. The term "antisense" refers to a DNA sequence whose sequence of deoxyribonucleotide residues is complementary to all or part of the sequence of deoxyribonucleotide residues in a sense strand. Thus, an "antisense" sequence is a sequence having the same sequence as the non-coding strand in a DNA duplex. With respect to RNA, the term "antisense" refers to a RNA transcript that is complementary to all or part of a target primary transcript or mRNA and that blocks the expression of a target gene by interfering with the processing, transport and/or translation of its primary transcript or mRNA. The complementarity of an antisense RNA or DNA may be with any part of the specific gene or transcript, i.e., at the 5' non-coding sequence, 3' non-coding sequence, introns, or the coding sequence.

The term "isolated" when used in relation to a nucleic acid, refers to a nucleic acid sequence that is identified and separated from at least one contaminant nucleic acid with which it is ordinarily associated in its natural environment. That is, an isolated nucleic acid is one that is present in a form or setting that is different from that in which it is found in nature.

The terms "sequence identity" or "amino acid identity" are used herein to describe the sequence relationships between two or more nucleic acid or amino acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions.

After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. It will be appreciated that a sequence having a certain % of sequence identity to a reference sequence does not necessarily have to have the same total number of nucleotides or amino acids (see e.g., microRNAs discussed above). Thus, a sequence having a certain level of "identity" includes sequences that correspond to only a portion (i.e., 5' non-coding regions, 3' non-coding regions, coding regions, etc.) of the reference sequence.

The present description uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Finally, as used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

EXAMPLES

The following examples set forth methods in accordance with the invention. It is to be understood, however, that these examples are provided by way of illustration and nothing therein should be taken as a limitation upon the overall scope of the invention.

Example 1

Wheat Cultivars and Growth Conditions

The following wheat (*Triticum aestivum* L.) cultivars were used in these Examples: "Bobwhite," "Newton," "Molly," "Iris," "Karl92," and "WGRC42." Bobwhite is a Spring wheat, containing no Hessian fly resistance (R) gene. Bobwhite was used for generation of transgenic plants for RNA interference (RNAi)-based Mds-1 knockdown, as described in Example 7. Newton is a winter wheat containing no Hessian fly R gene, and was used as a susceptible control in several studies. Molly and Iris are two isogenic wheat lines of Newton. Molly contains the R gene H13, whereas Iris contains the R gene H9. Karl92 is another wheat line containing no R gene, and used for RNAi-based Mds-1 knockdown. WGRC42 is a winter wheat that contains the R gene Hdic. Molly was used for overexpression of Mds-1 to determine the dominant effect of high level expression of Mds-1 on wheat susceptibility, as described in Example 10.

Wheat seedlings were grown in individual flats 52×36×10 cm in dimension, or 4-inch diameter pots. The Pro-Mix "BX" medium (Hummert International, Topeka, Kans., USA) was used as soil for growing wheat seedlings. Wheat seedlings were grown in either an AR-66L controlled environment chamber (Percival Scientific, Inc., Perry, Iowa, USA) or in a greenhouse as specified in individual experiments. The environmental chambers were programmed with a 16 h/8 h light/dark photoperiod at a light intensity of 800 $\mu E/m^2/s$, and under a temperature regime of 20° C./18° C. day/night with 70% relative humidity. Heat stress, where indicated in individual experiments, was delivered by adjusting temperature of the chambers with other conditions remaining unchanged. Winter wheat seedlings were vernalized in a cold chamber room at 4° C. with a 12 h/12 h light/dark photoperiod for 6 weeks.

Wheat Tissue Collection

For tissue collection in the present Examples, 10 mm of the second leaf-sheath at the feeding site (next to the base) was cut out after removing Hessian fly larvae. For non-transgenic experiments, samples contained tissues from a pool of 10 plants. For transgenic experiments, samples were collected from single plants and their tillers. The leaf-tissues were frozen in liquid nitrogen immediately after collection, and stored in a −80° C. freezer for later use. DNA, RNA, or protein samples were derived from the collected tissues separately.

Example 2

Hessian Fly Biotypes

In the present Examples, two Hessian fly populations (biotypes GP and vH13) were used for infestations. Biotype GP is avirulent to cultivars containing either H9 (Iris), H13 (Molly), Hdic (WGRC42), or other R gene. Biotype vH13 is virulent to H13 contained in Molly, but avirulent to other existing R genes. The GP biotype was maintained on Karl92 (a cultivar carrying no Hessian fly R gene) wheat seedlings. The vH13 biotype was maintained on Molly. Hessian fly stocks were stored as pupae at 4° C. in a cold room at the USDA-ARS Hard Winter wheat Genetics Research Unit at Kansas State University.

Hessian Fly Infestation and Phenotype Evaluation

Wheat seedlings were infested at one-leaf stage (full grown first leaf and second leaf just emerged) with eggs by confining Hessian fly adults with the plants using a cheese cloth tent or individual cages with a mesh screen. About five mated female adults were used per 20 plants, resulting in about 10-20 eggs per plant. It took 3-4 days for Hessian fly eggs to hatch. Neonate larvae migrate into wheat seedlings and live between leaf-sheaths at the crown of a plant as parasites. The initial attack time (also called larval infestation) was taken as the time when neonates reached the feeding site. Uninfested control seedlings were treated exactly the same way but without any Hessian flies.

Phenotypes of wheat seedlings were determined two to three weeks after initial larval infestation. Plant resistance (R) is defined in the Examples as normal wheat growth and death of Hessian fly larvae without development. Plant susceptibility (S) is defined in the Examples as stunted wheat growth and normal development of Hessian fly larvae.

Example 3

Powdery Mildew Infection and Phenotype Evaluation

For powdery mildew infestation, a mixed population of wheat powdery mildew *Erysiphe graminis* was used. *E.*

*graminis* was maintained on Bobwhite seedlings in growth chambers at a greenhouse at Kansas State University. Conidia of *E. graminis* were collected into water from lesions on plants with heavy infestation of the fungus. For inoculation, a conidia solution was uniformly sprayed onto plants with a small hand-spray inoculator, which were then placed in an environmental chamber for symptom development. Manifestations of infection were monitored visually in the course of its progression from conidia germination to the end of the fungus reproductive stage (~7-10 days). Host reactions were scored and recorded 7 to 10 days after inoculation, when the susceptible plants exhibited large legions of heavy infestation. Disease severity evaluation was based on a scale of 0 to 4 as described by Wang et al (2005), where 0 represents no visible symptoms except hypersensitive necrotic flecks; 1 represents sparse and tiny colonies with thin mycelia (hyphae) and very few conidia produced; 2 represents obvious colonies with moderately developed mycelia, but few conidia; 3 represents dense colonies with well-developed thick mycelia and abundant conidia, but colonies not merged each other; and 4 represents dense colonies with well-developed mycelia and abundant conidia, and most colonies merged together.

Example 4

Analysis Methods

DNA and RNA Extraction

Genomic DNA was extracted from wheat tissues according to a modified cetyl trimethylammonium bromide (CTAB) procedure as described by Doyle and Doyle (1987). The buffer contained 2% CTAB, 100 mM TrisHCl pH=8, 20 mM EDTA, 1.4M NaCl, 0.2% β-mercaptoethanol (added just before use), and 0.1 mg/mL proteinase K (added just before use). The tissues (~100 mg) were collected in a 1.7 ml microfuge tube and frozen in liquid nitrogen. The frozen tissues were thoroughly ground to powder with a chilled pellet pestle driven by a cordless motor (Fisher Scientific, Pittsburgh, Pa., USA) and then homogenized with 700 μL 65° C. CTAB buffer, followed by incubating in a 65° C. water bath (with shaking) for 1 hour. The homogenate was extracted once with 700 μl chloroform-isoamyl alcohol (24:1), mixing gently but thoroughly, followed by a 5 min. centrifugation in a micro-centrifuge at around 6,000×g. The aqueous phase was transferred to a new tube with a wide bore pipet and DNA was collected by adding ⅔ volumes cold isopropanol. The solution was then mixed gently to precipitate nucleic acids, followed by a 5 min. centrifugation in a micro-centrifuge at around 6,000×g. After removing supernatant, the DNA pellet was washed with 70% cold ethanol, and the DNA sample was then resuspended in 1 ml TE (10 mM Tris-HCl, 1 mM EDTA, pH 7.4), and stored at 4° C. for later use.

Plasmid DNA was extracted and purified using a QIAprep Spin Miniprep Kit (Qiagen Inc., Valencia, Calif., USA) from overnight bacterial cultures in Luria-Bertani medium containing antibiotics at 37° C. in a shaking incubator according to the protocol provided by the manufacturer.

Total RNA was extracted from wheat tissues using a TRI Reagent™ according to the procedure provided by the manufacturer (Molecular Research Center, Inc., Cincinnati, Ohio, USA). The RNA samples were further purified through an RNease kit according to the manufacturer's instruction (Qiagen Inc., Valencia, Calif., USA). Concentrations of the DNA and RNA samples were measured with a NanoDrop-1000 Spectrophotometer (NanoDrop Technologies, Wilmington, Del., USA).

Southern and Northern Blot Analyses

Southern blot analyses in the present Examples were carried out as follows. Fifteen μg of extracted genomic DNA was digested with 120 units of the restriction enzyme Hind III (Promega, Wis., USA) in a 30-μl solution at 37° C. for 5 h. Next, the enzymatic activity was inactivated by incubating the reaction mixture at 65° C. for 30 min. Fifteen μl distilled water and 5 μl loading buffer were then added to the reaction mixture. After mixing, the samples were loaded onto a 0.8% agarose gel. The gel was run for electrophoresis in TBE buffer under 120 mV for two hours. DNA on the gel was then transferred onto a Genscreen membrane (Perkin Elmer Life Science Inc., Boston, Mass.). The DNA was cross-linked to the membrane by baking the blot at 80° C. for 2 h. The membranes were then hybridized to a probe derived from the full length Mds-1 gene. The probe was generated using a random labeling kit from Stratagene (La Jolla, Calif.). Hybridization was carried out overnight at 42° C. in a plastic bag containing a 15 ml hybridization solution (10% dextran sulfate/1% SDS/1M NaCl, pH 8.0). After hybridization, the membranes were washed twice with 2× saline-sodium citrate buffer (SSC) at room temperature for 30 minutes, twice with 2×SSC plus 1% SDS at 65° C. for 30 minutes, and then twice with 0.1×SSC plus 1% SDS at room temperature for 30 minutes. The membranes were then exposed to Kodak SR-5 X-ray film overnight.

For Northern blotting, equal amounts (7.5 μg) of total RNA per sample were separated by formaldehyde-agarose gel electrophoresis, and blotted onto GeneScreen membranes. Cross-linking, hybridization, washing, and exposure were each carried our as described for Southern blotting above.

Production of Recombinant Protein and Polyclonal Antibody

A full length recombinant protein with a C-terminal his-tag (7 Histidines) was provided by GenScript (Piscataway, N.J., USA). The same company used the recombinant protein as an antigen to produce the polyclonal antibody in rabbits. The polyclonal antibody was affinity-purified with immobilized antigen.

Western Blot Analysis

Protein extracts were prepared from samples by homogenizing wheat tissues in 50 mM Tris-HCl buffer (pH 8.0) containing a protease inhibitor cocktail (Sigma-Aldrich, St. Louis, Mo., USA), followed by centrifugation at 13,200 rpm for 20 min at 4° C. The supernatant was then collected, and the protein concentration was measured using a bicinchoninic acid kit (Sigma-Aldrich). For electrophoresis, 180 μg of protein was loaded onto the Nupage 12% Bis-Tris gel and separated using Xcell surelock electrophoresis cells (Invitrogen, Carlsbad, Calif., USA). Proteins on the gel were transferred to a PVDF membrane (immobilon-PSQ, Millipore) using an Xcell II blot module (Invitrogen, Carlsbad, Calif., USA) at 21 V for 1.30 h. The membrane was blocked using 5% (w/v) nonfat milk in Tris Buffer Saline Tween 20 (TBST, 50 mM Tris-HCl, pH 8.0, 150 mM NaCl, and 0.1% Tween 20) for 1 h at 4° C. The PVDF membrane was then incubated overnight at 4° C. with primary antibody-HRP conjugation (0.5 ug/ml of 2% milk/TBST). Next, the membrane was washed three times in TBST and incubated for 1 min. with HRP chemiluminescent detection reagents (invitrogen, Carlsbad, Calif., USA). The excess reagent was then poured off, and the membrane was exposed to film for 4 h.

To determine the gel loading, the gel after transfer was stained with Coomassie blue for 1 h. Images were taken after the gel de-stained to visualize protein bands.

Example 5

Identification of Genes Involved in Resistant or Susceptible Interactions

In previous work, the Affymetrix GeneChip® Wheat Genome Array was used to identify genes that are either up- or down-regulated in different wheat genotypes during either incompatible (resistant plants) or compatible (susceptible) Hessian fly interactions (Liu et al. 2007). A large number (1,227) of probe sets detected alterations in transcript abundance in wheat plants attacked by Hessian flies (Liu et al. 2007).

In this Example, the resulting array data guided the knockdown of various genes listed in Table 1 using a virus-induced gene silencing (VIGS) approach. The effect of these genes or gene combinations on wheat resistance or susceptibility to Hessian fly attack was then determined. Three groups of heat shock protein (Hsp) genes were chosen for VIGS: Hsp70, Hsp90, and Small Hsp.

TABLE 1

Virus-induced gene silence (VIGS) of heat shock protein (Hsp) genes.

| Affymetrix probe ID | GenBank accession | Putative identification | S fold change | R fold change | Gene silence confirmation | Plant phenotype |
|---|---|---|---|---|---|---|
| Hsp70 | | | | | | |
| Ta.30802.1.A1_at | CA702016 | HSP70 | 4.8 | 0.42 | PCR | S |
| Ta.24515.1.S1_at | AF005993 | HSP70 | 2.6 | 0.84 | PCR | S |
| Ta.10259.1.S1_at | BJ265952 | HSP70 | 7.3 | 3.1 | PCR | S |
| Hsp90 | | | | | | |
| Ta.2502.3.A1_at | BJ306224 | HSP90-1 | 0.91 | 0.87 | PCR | S |
| Ta.2502.2.A1_x_at | CD865828 | HSP90-2 | 0.87 | 0.83 | PCR | S |
| Ta.28735.1.S1_a_at | BJ250459 | HSP90-like | 1.23 | 1.29 | PCR | S |
| Ta.28235.1.A1_s_at | BJ214932 | GRP90 | 1.17 | 1.1 | PCR | S |
| | | | | | | S |
| Small Hsp | | | | | | |
| Ta.204.1.S1_at | AF104108 | HSP23.6 | 9.7 | 0.91 | PCR | S |
| Ta.24332.1.S1_at | CD453475 | HSP16.9 | 30.3 | 0.06 | PCR, Northern blot | R |

Virus-Induced Gene Silencing (VIGS)

Figure 1B:
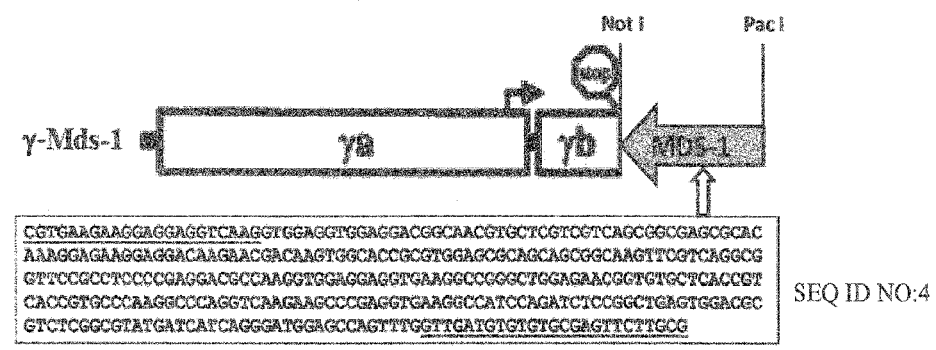
FIG. 1B is a schematic representation of the modified γ subgenome by inserting a 338 bp fragment of the target gene Mds-1 in antisense orientation, and the sequence of the inserted Mds-1 fragment (SEQ ID NO:4) from Example 5.

Barley stripe mosaic virus (BSMV), a tripartite single-stranded positive sense RNA virus, was used for VIGS (FIG. 1A). The BSMV vectors used for VIGS were originally obtained from Dr. Andrew O. Jackson at UC Berkeley (Petty et al., 1989), and were constructed following a protocol described by Holzberg et al. (2002) and Scofield et al (2005). FIG. 1A is a schematic representation of the BSMV genome and Mds-1 VIGS construct for transient gene silencing. FIG. 1A shows the genomic RNAs of BSMV consisting of 3 subgenomes (tripartite α, β, γ) (adapted from Holzberg et al. 2002). The γ vector was reconstructed to include PCR-ready cloning sites according to Campbell and Huang (2010), by first amplifying a 338 bp 3'-fragment of Mds-1 gene via PCR using a DNA polymerase AccuPrimer™ Pfx SuperMix (Invitrogen, CA, USA) with a pair of specific primers (Mds-1La, 5'-CGTGAAGAAGGAGGAGGTCAAG (SEQ ID NO:5), and Mds-1R, 5'-CGCAAGAACTCGCACACA-CATC (SEQ ID NO:6)). The PCR fragment was then purified with a QIAquick PCR purification Kit (Qiagen Inc., Valencia, Calif., USA) and inserted directly into the γ genome by ligation with T4 DNA ligase as shown in Figure S1A in an antisense orientation. FIG. 1B shows the modified γ subgenome with the target gene Mds-1 in the antisense orientation (sequence of inserted Mds-1 fragment indicated below genome, SEQ ID NO:4). BSMV plasmids α, β, and γ-Mds-1 were prepared from an overnight culture (LB+100 mg/L carbinecilin) at 37° C. with shaking at 225-250 rpm, and purified using a QIAGEN QIAprep Centrifuge Miniprep Kit (Qiagen Inc., Valencia, Calif., USA) according to the manufacturer's instructions. The purified plasmids were further lineralized by restriction of the following endonucleases, α-Mds-1 with MluI, β-Mds-1 with SpeI, and γ-Mds-1 with BssHII, respectively. The linearized plasmids were then used for in vitro transcription.

In Vitro Transcription of Viral RNAs and Plant Inoculations for VIGS

Infectious RNA transcripts were synthesized in vitro using a mMessage mMachine T7 transcription kit (Ambion, Austin, Tex., USA) from linearized α, β, and γ Target plasmids following the procedure described by Scofield et al (2005). The in vitro transcription reaction typically resulted in 1 to 1.5 μg/μL final concentration of RNA. The silencing BSMV inoculum was made by combining an equal molar ratio of α, β, and γ Target transcripts with excess inoculation buffer containing a wounding agent (FES). One microliter of each of the in vitro transcription reaction products for the α, β, and γ subgenome RNAs were combined and transferred to 22.5 μL of FES. This RNA mixture was then applied to the plants by rub inoculation. The second leaf of each ten-day old wheat seedling was inoculated with the synthesized RNA inoculum. The plants were visually assessed for viral infection symptoms 8 days post-BSMV inoculation, and then infested with Hessian fly. Phenotypic evaluation was conducted 10 days after Hessian fly larval infestation. Gene silencing by VIGS was confirmed by quantitative real-time PCR and Northern blot analysis. Two wheat cultivars, Newton and Karl92, both of which contain no Hessian fly R gene, were chosen for VIGS and both of them gave identical susceptible or resistant phenotypes.

Results

Knockdown of genes encoding HSP90s, HSP70s, and a HSP23 did not cause any apparent changes in phenotype of wheat seedlings in tennis of interactions with Hessian fly.

However, knockdown of a gene corresponding to an expression sequence tag (EST) (Genbank accession CD453475) made wheat cultivars containing no R gene resistant to Hessian fly. Since the expression of this gene is required for wheat susceptibility to Hessian fly attack, this gene was named *Mayetiola destructor* susceptibility one (Mds-1) gene.

Figure 2:
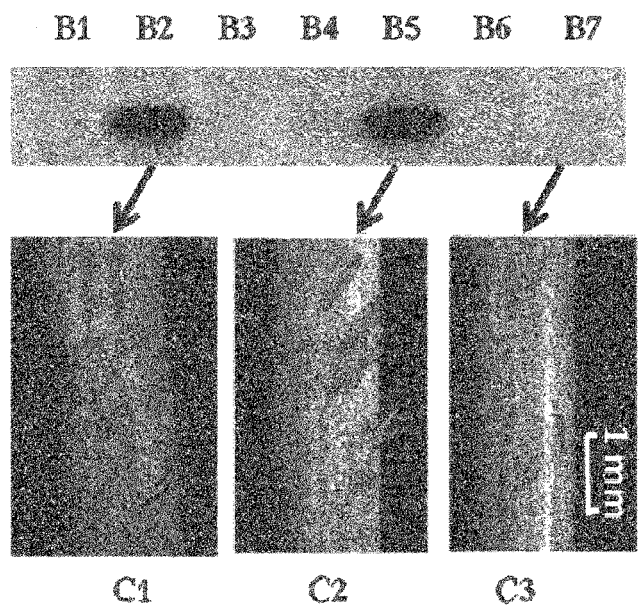
FIG. 2 is a Northern blot analysis of the VIGS effect on Mds-1 transcript abundance, along with photographs of corresponding phenotypes of Hessian fly larvae on control and VIGS-treated plants.

FIG. 2 shows Northern blot analysis of the VIGS effect on Mds-1 transcript abundance (B1-B7) along with the corresponding phenotype (C1-C3) of Hessian fly larvae on control and VIGS-treated plants. Black arrows between panels indicate a correlation between Mds-1 expression and Hessian fly larval phenotypes. High levels of Mds-1 transcripts were associated with larval growth and development, whereas a low level of Mds-1 transcripts was associated with larval death. Pink arrows point to representative live or dead Hessian fly larvae. B1 indicates is an image from an RNA sample extracted from the feeding site of a pool of five control plants with no VIGS and no Hessian fly infestation. Mds-1 transcripts were not detectable, indicating that Mds-1 was not expressed at the tissue corresponding to the Hessian fly feeding site under normal growth conditions. B2 indicates an image from a sample of five plants with no VIGS, but with Hessian fly infestation. Abundant transcripts of Mds-1 were detected, indicating that Mds-1 was induced by Hessian fly attack. B3 indicates an image from another control sample of five plants with no VIGS and no Hessian fly infestation. B4 indicates an image of a sample of five plants treated with the empty VIGS vector (containing no Mds-1 insert) and with no Hessian fly infestation. A low level of Mds-1 transcripts were detected, which could be due to a stress response to the VIGS BSMV inoculation itself. B5 indicates an image from a sample of five plants treated with the empty VIGS vector and with Hessian fly infestation. Abundant Mds-1 transcripts were detected, indicating that the VIGS vector itself did not inhibit the induction of Mds-1 by Hessian fly attack. B6 indicates an image from a sample of five plants treated with the Mds-1 VIGS construct, but without Hessian fly infestation. Mds-1 transcripts were not detectable. B7 indicates an image from a sample of five plants treated with the Mds-1 VIGS construct and with Hessian fly infestation. Again no Mds-1 transcripts were detectible, indicating that Mds-1 VIGS can either remove Mds-1 transcripts induced by Hessian fly attack, or prevent the induction of Mds-1 by Hessian fly attack.

C1-C3 indicate photographs of a sample of the tested plants. C1 is a photograph showing live larvae on a control plant. C2 is a photograph showing live larvae on a plant treated with the empty VIGS vector. C3 is a photograph showing dead larvae on a plant treated with the Mds-1 VIGS construct.

Example 6

Cloning of Mds-1

Based on the CD453475 EST sequence identified in Example 5, a full length coding region (cDNA) of Mds-1 was cloned following a rapid-amplification-of-cDNA-ends (RACE) approach. Poly A+ mRNA was purified from 400 μg of total RNA, which was isolated from Hessian fly-infested Newton wheat using the PolyATract® mRNA Isolation System III from Promega Corporation (Madison, Wis., USA). Reverse transcription was performed using the SMART™ RACE cDNA Amplification Kit (Clontech Laboratories, Inc., Mountain View, Calif., USA), with an adapter oligo (GGG) ligated to the 5'-end of cDNAs during reverse-transcription. Amplification of the 5'-cDNA upstream region was carried out using an adapter-specific primer named NUP A (5'-AAGCAGTGGTATCAACGCAGAGT (SEQ ID NO:10) and a gene-specific primer named Mds-1R (5'-CGCAAGAACTCGCACACACATC (SEQ ID NO:6)), synthesized according to the CD453475 EST sequence). The Mds-1R primer is located 45 bp downstream of the stop codon at the 3'-untranslated region (UTR). Amplification of the 3'-end was carried out using an adapter-specific primer NUP-A and a gene-specific primer Mds-1 La (5'-CGT-GAAGAAGGAGGAGGTCAAG (SEQ ID NO:5)). PCR amplification was carried out using the high-fidelity and high-specificity DNA polymerase AccuPrimer™ Pfx SuperMix (Invitrogen, Carlsbad, Calif., USA) according to the protocol provided by the manufacturer, and performed in a thermal cycler using initial denaturation at 94° C. for 5 min., followed by 36 cycles of 1.0 min. at 94° C., 1.0 min. at 58° C., and 2.0 min. at 72° C. One additional extension cycle was performed for 10 min. at 72° C.

Next, the RACE product was gel-purified using a GeneClean® Turbo for PCR Kit (Qbiogene, Inc., Carlsbad, Calif., USA), and then cloned directly into the vector pCR®II-TOPO® using a TOPO TA Cloning® kit (Invitrogen, Carlsbad, Calif., USA) following the protocols provided by the manufacturers. After transformation and bacterial colony development, Mds-1-positive clones were identified using PCR with the primer pair NUP A and Mds-1R (as used in RACE). Positive clones were sequenced using the universal M13 Forward and Reverse primers contained in the cloning vector on a 3730 DNA Analyzer (Applied Biosystems, Foster City, Calif., USA) at the Sequencing Facility of Kansas State University.

Figures 3, 4:
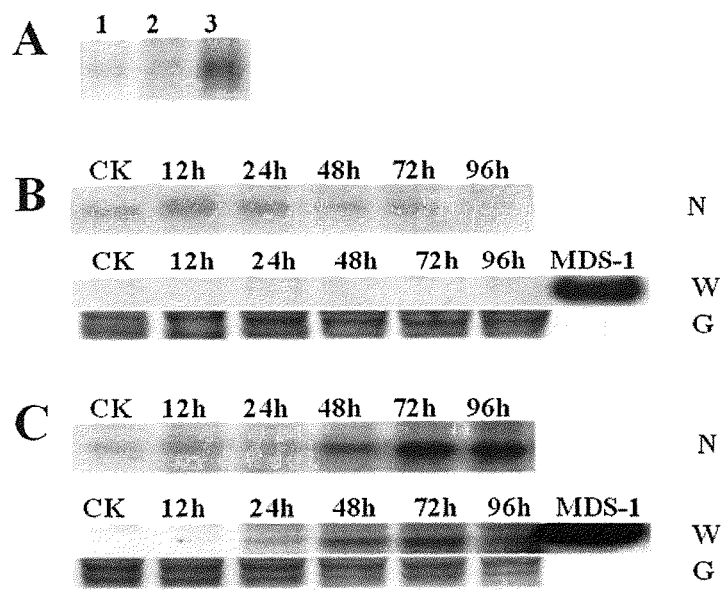
FIG. 3 shows the conservation of Mds-1 homologues from different organisms: TA_Hsp16.9 (Accession No. 1GME_A) from *Triticum Aestivum*; OS_Hsp16.9 (Accession No. P27777) from *Oryza sativa japonica*; AT_Hsp17.6 (Accession No. CAA34208) from *Arabidopsis thaliana*; and SL_RSI2 (SGN-U578930 Tomato 200607 #2) from *Solanum lycopersicum*. The alignment was generated with clustalW and printed with BoxShade.
FIG. 4 depicts the results from blotting analysis of tissue expression and response of Mds-1 to Hessian fly attack in wheat seedlings during incompatible and compatible interactions from Example 6.

The cloned Mds-1 cDNA with the primer pair NUP A and Mds-1R consisted of a 627 base pair (bp) sequence, with a 101 bp 5'-UTR, a 456 bp coding region, and a 70 bp 3-UTR. To clone the Mds-1 gene, genomic DNA was extracted from two wheat cultivars, Newton and Bobwhite, separately. A new primer (Mds-1-Lb, 5'-ACCTGCGACCCAATCCA-GAAC (SEQ ID NO:7)) covering the 5'-UTR end of the Mds-1 cDNA was synthesized. PCR amplification was conducted using the primer pair Mds-1-Lb and Mds-1R with wheat genomic DNA as the template. Cloning and sequencing or the PCR fragment was done the same way as described for the cDNA cloning above. There was no difference between the sequences derived from Newton and Bobwhite genomic DNA samples. The genomic DNA sequence was identical to the cDNA sequence and no intron was found within the Mds-1 gene. The full length Mds-1 gene, coding sequence, and protein sequences are shown in SEQ ID NOs:1-3, respectively. The gene encodes a protein of 151 amino acids that shares 96% identity with a previously characterized wheat protein, HSP 16.9 (FIG. 3). HSP (also called HSP17-20 in other species) is evolutionarily conserved with an α-crystallin domain.

Tissue expression and response of Mds-1 to Hessian fly attack in wheat seedlings during compatible and incompatible interactions was then analyzed. Tissues were then collected for analysis. A Northern blot analysis detected very low level of transcript in leaf-sheaths, where Hessian fly larvae feed, under normal growth conditions; but abundant transcript was detected in developing seeds under normal conditions. These results are shown in FIG. 4A: (1) leaf-blades; (2) leaf-Sheaths (tissues corresponding to Hessian fly feeding site); and (3) developing seeds (five days after heads out of sheath). Transcripts were barely detectable in wheat leaf-blades and leaf-sheaths, but were abundantly expressed in developing seeds.

We then examined the impact of avirulent and virulent Hessian fly larvae on Molly. Incompatible interactions were initiated by infesting Molly seedlings with an Hessian fly avirulent biotype (biotype GP), whereas compatible interactions were initiated by infesting Molly seedlings with a virulent biotype (biotype vH13), followed by recombinant protein, antibody and blotting analyses. Attack by avirulent larvae did not affect the abundance of either Mds-1 transcript or protein (FIG. 4B), whereas attack by virulent larvae elevated the levels of both Mds-1 transcript and protein (FIG. 4C). FIG. 4B shows the response of Mds-1 to Hessian fly attack in plants during incompatible interactions at the transcript and protein levels as determined by Northern (N) and Western (W) blot analyses. "G" represents a gel image of the protein bands in the region where Mds-1 protein is located. The image was derived by staining the gel after protein transfer for blot analysis. "CK" indicates un-attacked control plants, whereas the indicated times represent plants attacked by avirulent Hessian fly larvae for time periods ranging between 12 h and 96 h, as indicated. "MDS-1" represents a full length of recombinant Mds-1 protein. There was no significant change at the transcript level in wheat seedlings following avirulent larval attack. Mds-1 protein was not detectable at all time points. FIG. 4C shows the response of Mds-1 to Hessian fly attack in plants during compatible interactions as determined by Northern (N) and Western (W) blot analyses.

Example 7

Generation of Mds-1 Knockdown Wheat

Figure 5A:
FIG. 5A is a schematic representation of the expression construct derived from the pANDA-mini vector with inverted Mds-1 sequences flanking the gus linker from Example 7.

To further confirm the essentiality of elevated levels of Mds-1 expression for wheat susceptibility, transgenic wheat was generated with a construct expressing double-stranded RNA (dsRNA) for RNA interference (RNAi)-based gene silencing shown in FIG. 5A. The construct with an inverted repeat (IR) was made according to the Gateway system described by Miki and Shimamoto (2004; 2005). A 338-bp fragment of the Mds-1 gene (SEQ ID NO:4) was amplified in the same way as described in Example 5 for VIGS. The PCR product was first subcloned into an entry vector pENTR™/D-TOPO® using the pENTR™ directional TOPO cloning kits (Invitrogen, Carlsbad, Calif., USA). The final RNAi-based knockdown construct was made by recombination via a LR clonase reaction using a Gateway® LR clonase enzyme mix (Invitrogen) between the entry vector carrying the Mds-1 gene fragment and the pANDA-mini vector, from which the identical gene fragment was cloned into both sides flanking the 920-bp gus linker of the pANDA-mini vector in the antisense and sense orientations, respectively. The transcribed RNA contained a hairpin sequence that forms dsRNA. Clones with expected inserts were confirmed through PCR and sequencing.

For Mds-1 knockdown, Bobwhite cultivars were co-bombarded (using a 1:1 molar ratio) with the pANDA-mini RNAi construct and the pAHC20 vector (contains the bar gene for selection of resistance to the herbicide ammonium glufosinate ("Liberty")) using microprojectile bombardment. Immature embryos were isolated 10-14 days post-anthesis and cultured as described by Altpeter et al. (1996). Approximately 10-14 days post anthesis, spikes were collected and immature caryopses were sterilized in a solution containing 20% commercial bleach and 0.1% Tween-20 for 20 min., and then rinsed three times with sterile, distilled water. Immature embryos were excised and placed on CM4 medium, with the embryo-side in contact with the medium for 5-7 days in the dark at 25° C. to initiate callus formation. Induced embryogenic calli were transferred to CM4+osmaticum (0.2M mannitol and 0.2M sorbitol) 4-16 h prior to genetic transformation. Genes were introduced into embryogenic calli with the particle inflow gun. Sixteen hours after transformation, Galli were placed on a selection medium (5 mg/liter glufosinate) for 10 days and a shoot-production medium for 2 weeks, and then transferred to an elongation and rooting medium for 2 weeks. Once roots formed, the plants were transferred to soil. Recovered plants were initially screened for the presence of the selectable marker gene (i.e., the bar gene), by applying a freshly prepared aqueous solution of 0.2% Liberty (AgEvo USA, Pikeville, N.C.) to the midlamina portion (2.5 cm long) of the second or third youngest leaf.

The transgenic plants with confirmed herbicide resistance were then analyzed for the presence of the Mds-1 construct. DNA was extracted from the leaves of the Liberty resistant plants following the CTAB procedure as described in Example 4. Presence of the Mds-1 construct was detected by PCR using a Master Mix (Promega, Madison, Wis., USA) in a 25 μL reaction mixture that contained 100 ng of the wheat DNA as a template and 0.4 μM of each primer in the following combinations. To detect the presence of the antisense Mds-1 insert, the gus linker forward primer, Gus-F (5'-CACGTAGTCCGCATCTTCA (SEQ ID NO:11)) and the common gene specific reverse primer, Mds-1R (5'-CGCAAGAACTCGCACACACATC (SEQ ID NO:6)) were used in a PCR reaction. The resulting PCR fragment was a 520 bp sequence. To detect the presence of the sense Mds-1 insert, the gus linker reverse primer, Gus-R (5'-GTGGAGTGAAGAGTATCAGTGTGC (SEQ ID NO:12)) and the gene specific reverse primer Mds-1R (5'-CGCAAGAACTCGCACACACATC (SEQ ID NO:6)) were used in a PCR reaction. The resulting PCR fragment was a 620 bp sequence. To detect the presence of the bar gene, the bar forward primer, UbiABF (5'-CCTGCCTTCATACGCTATTTATTTGC (SEQ ID NO:28)) and the bar reverse primer, BarABR (5'-CTTCAGCAGGTGGGTGTAGAGCGTG (SEQ ID NO:29)) were used in a PCR reaction. The resulting PCR fragment was a 616 bp sequence. PCR products were resolved in 1.5% w/v agarose gels and visualized by ethidium bromide staining.

Results

From a total of 39 herbicide-resistant transformation clones, 25 independent transformants containing the Mds-1 dsRNA construct were obtained as shown in Table 2, below.

TABLE 2

Summary of Bobwhite transgenic plants containing the Mds-1 knockdown construct*

| Plant | Bar | GOIa | GOIb | PHF | PPM | Seeds |
|---|---|---|---|---|---|---|
| 150a, b, c, t | + | + | + | R | NA | yes |
| 152a, b, c, d, t | + | + | − | R | NA | yes |
| 228a, b, c | + | + | − | R | NA | yes |
| 358a, t | + | + | + | R | NA | yes |
| 432 | + | + | + | R | NA | yes |
| 439 | + | + | + | S | NA | yes t |
| 523a, b | + | + | + | aR, bS | NA | yes a, t |
| 716a | − | − | − | S | NA | dead |
| 910 | − | − | − | S | NA | dead |
| 990a | − | − | − | S | NA | yes t |
| 1629 | − | − | − | S | S | yes |
| 1630 | + | + | + | R | MR | yes |

TABLE 2-continued Summary of Bobwhite transgenic plants containing the
Mds-1 knockdown construct*

| Plant | Bar | GOIa | GOIb | PHF | PPM | Seeds |
|---|---|---|---|---|---|---|
| 1631 | + | − | − | S | S | yes |
| 1639a, b, c | ab+c− | ab+c− | ab+c− | abR | MR | yes |
| 1703 | + | + | + | R | MR | yes |
| 2030 | + | + | + | R | MR | yes |
| 2034 | − | − | − | S | S | dead |
| 2053 | + | + | − | R | MR | yes |
| 2059 | + | + | + | S | S | dead |
| 2060 | − | − | − | S | S | dead |
| 2061 | − | − | − | S | S | heat dead |
| 2065 | + | + | − | R | MR | yes |
| 2087 | − | − | − | S | S | dead |
| 2089 | + | + | + | R | MR | heat dead |
| 2090 | + | + | + | R | MR | yes |
| 2095 | + | + | + | R | MR | yes |
| 2101 | + | + | + | R | MR | heat dead |
| 2123 | − | − | − | S | S | dead |
| 2129 | + | + | + | R | MR | yes |
| 2164a, b, c, d | + | + | + | R | MR | yes |
| 2170 | − | − | − | S | S | yes |
| 2217a, b | − | − | − | S | S | dead |
| 2222 | + | + | + | S | S | dead |
| 2270 | + | + | + | S | S | yes |
| 2322 | + | + | − | S | S | dead |
| 2355 | + | + | + | R | MR | yes |
| 2357 | + | + | + | R | MR | yes |

*The letters after a transgene number represent different tillers when the plants were infested with Hessian fly or powdery mildew.
Bar, GOIa, and GOIb represent PCR detection results of the presence of the Bar gene (herbicide resistance), inserted gene at antisense, and sense orientation, respectively, in transgenic plants using a vector primer and a gene-specific primer as described herein. The negative "−" symbol indicates no PCR amplification at all.
The positive symbol "+" represents the detection of a DNA fragment with the expected size.
NA means not applicable or not determined.
PHF represents resistant (R) or susceptible (S) phenotypes of the transgenes to Hessian fly infestation.
PPM represents resistant or susceptible phenotypes of transgenes to powdery mildew infection.
Seeds represents transgenic plants that produced seeds successfully (yes) or did not reach the seed production stage (dead).
MR represents moderate resistance.
"Heat dead" represents plants were dead due to a malfunction of an overheating growth chamber, whereas "disposed" represents plants were disposed before they reached the flowing stage.

Figure 5B:
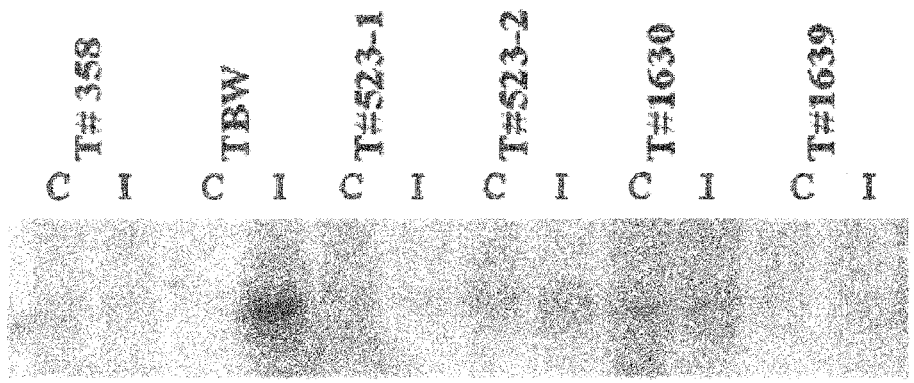
FIG. 5B depicts the results from Northern blot analysis of five independent Bobwhite transgenic lines T#385, T#523-1, T#385-2, T#1630, T#1639, and an empty-vector transgenic Bobwhite (TBW) as control from Example 7.
Figure 5C:
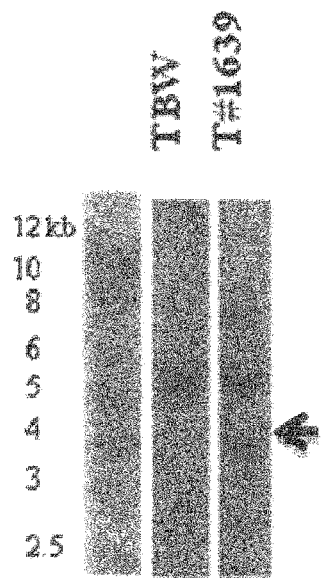
FIG. 5C depicts the results from Southern blot analysis of transgenic line T#1639 and TBW from Example 7.

Most (80%) of the Mds-1 construct-positive transformants had the Mds-1 gene knocked down (Table 2, FIGS. 5B and 5C). FIG. 5B is the Northern blot analysis of five independent Bobwhite transgenes (T#385, T#523-1, T#385-2, T#1630, T#1639), and an empty-vector transgenic Bobwhite (TBW) as control. RNA samples were extracted from uninfested controls (C) and infested (I) plants. Mds-1 was induced in TBW by Hessian fly attack, but the induction was inhibited in the RNAi-transgenes. FIG. 5C is the Southern blot analysis of genomic DNA samples extracted from TBW and T#1639, digested with Hind III, and probed with the full length Mds-1. The extra band in T#1639 indicated by an arrow on the right represents the construct integrated into the wheat genome.

Figure 6:
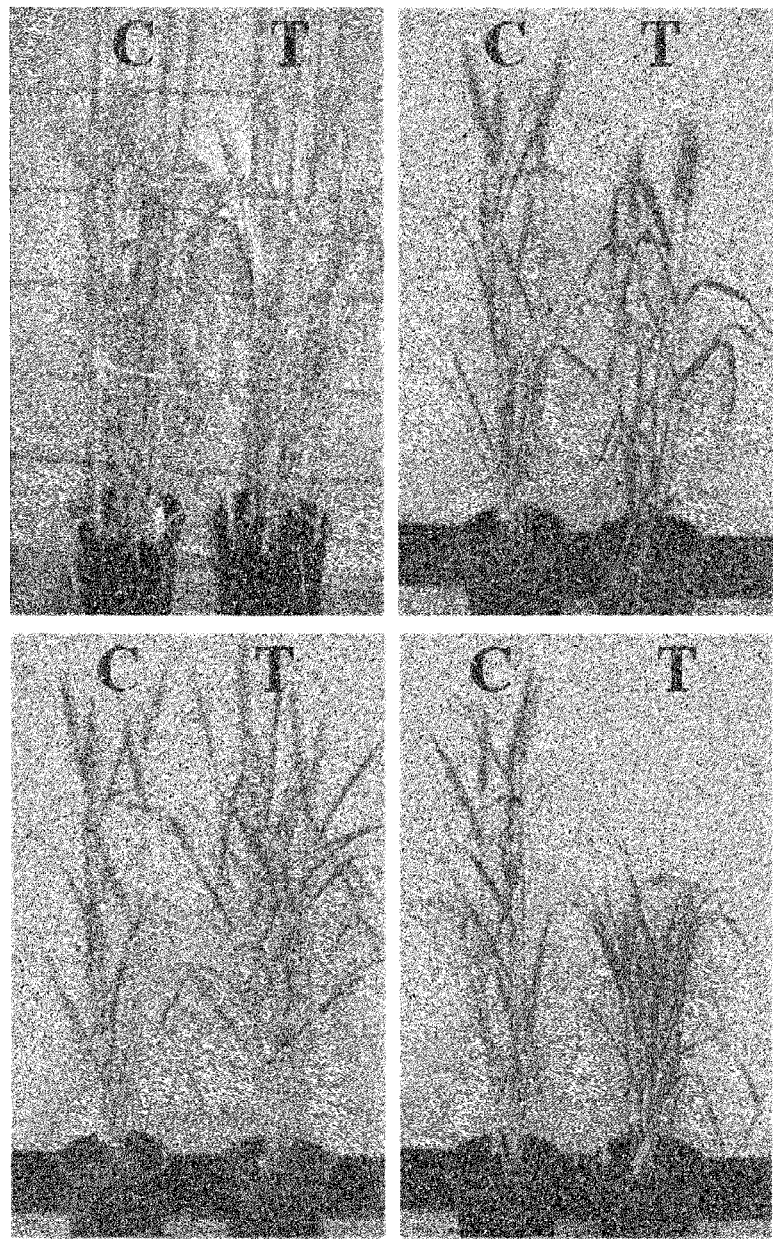
FIG. 6 shows photographs of transgenic (T) Bobwhite with Mds-1 knocked down as compared to control (C) plants from Example 7.
Figure 7A:
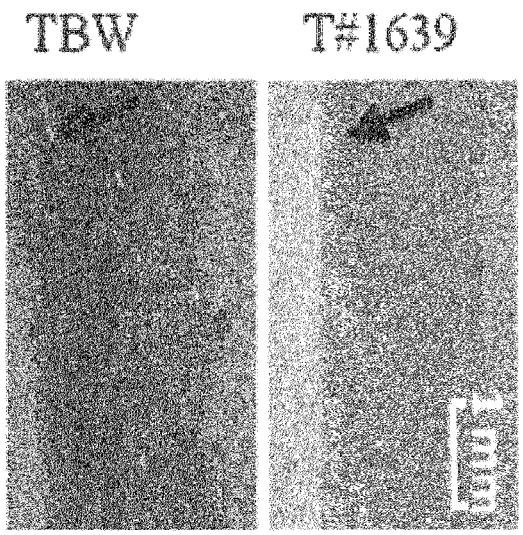
FIG. 7A is a photograph of Hessian fly larvae growing on transgenic line T#1639 and TBW from Example 8.
Figure 7B:
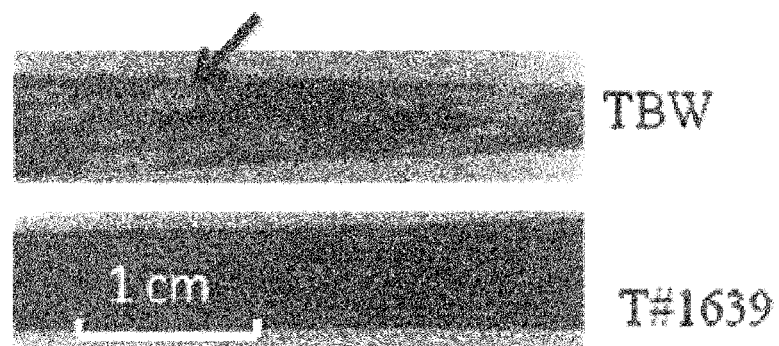
FIG. 7B is a photograph of powdery mildew growing on transgenic line T#1639 and TBW from Example 8.

Transgenic plants with Mds-1 knocked down showed various phenotypes, including reduced height and sterility, but some of the transgenic (T) plants were indistinguishable from non-transgeic controls (C) in growth chambers (FIG. 6).

Example 8

Susceptibility of Mds-1 Knockdown Wheat

Transgenic plants generated according to Example 7 were subjected to attack by the Hessian fly, as described in Example 2. All plants with the Mds-1 gene knocked down lost susceptibility to the Hessian fly (Table 2, FIG. 7A). FIG. 7A shows photographs of the phenotypic differences between Hessian fly larva on control (TBW) and Mds-1-knockdown wheat (T#1639). Arrows point to either a live (full grown) on the TBW control or dead (reddish and skinny) larva on the Mds-1 knockdown T#1639 transgene.

Since wheat resistance mediated by R genes exhibits features of penetration resistance to fungal pathogens, we also tested if the knockdown of Mds-1 gene prevented susceptibility of plants to powdery mildew. Wheat seedlings with Mds-1 knocked down were inoculated with powdery mildew (*Blumeria graminis* f. sp *tritici*) at the seedling stage or when the plants reached the flowering stage, as described in Example 3. Plants that lost susceptibility to Hessian fly also lost susceptibility to powdery mildew (Table 1 and FIG. 7B). FIG. 7B shows photographs of the phenotypic differences between powdery mildew on control and Mds-1-knockdown wheat. The fungus grew into full lesions (a representative lesion pointed by an arrow) on the TBW control, but produced limited lesions with much slower growth on the Mds-1-knockdown T#1639 transgene.

Example 9

Effect of Temperature on Mds-1 Expression

Most if not all Hessian fly R genes so far identified in wheat are temperature sensitive, meaning that plants with an R gene lose resistance when exposed to high temperatures (e.g., 30° C. to 37° C., depending on the particular R gene) for a certain period of time. Accordingly, the effect of high temperatures on Mds-1 expression (FIGS. 8A-B(a)) and the correlation between the levels of Mds-1 expression and wheat susceptibility (FIG. 8B(b)) were examined. Hessian fly biotype GP was used for infestations. Plants were subjected to heat stress and infested at different points as described above and herein.

FIG. 8 shows the Mds-1 expression levels and plant susceptibility results. FIG. 8A shows Northern blot and phenotypic analyses of heat-stressed plants and its effect on Mds-1 expression. Molly seedlings at 20° C. were infested with/without adult Hessian flies. One day before larval Hessian fly hatch, some of the infested plants were moved to growth chambers set at 30° C., 35° C., or 40° C. The phenotypes of control and heat-stressed plants are indicated in the Figure underneath the blot: CK—uninfested control, R—resistant, S—susceptible, and D—death of both plants and larva. Plants heated to 40° C. were over-stressed resulting in the death of both the plants and the insects. Mds-1 was upregulated in wheat leaf-sheaths under heat stress in both resistant and non-resistant wheat genotypes. Wheat seedlings of Molly growing at 35° C. had 10 fold or more Mds-1 transcripts and protein than plants growing at 20° C. did.

FIG. 8B shows the decay of heat-induced Mds-1 transcript and protein, and restoration of plant resistance. FIG. 8B(a) shows the results from Mds-1 induction in Molly grown at 37° C. for 6 h, 12 h, 24 h, 48 h, and 72 h, respectively. Total RNA and proteins were extracted and analyzed via Northern (N) and Western (W) blots. "MDS-1" represents the full length recombinant protein. The letter "G" represents a Coomassie blue-gel image corresponding to the region where Mds-1 was located from the same gel stained after protein transfer for Western blotting. To determine if elevated levels of Mds-1 transcript and protein at higher temperatures were correlated with wheat susceptibility, Molly plants were then grown at 37° C. for a given time period to induce Mds-1, and the plants were then shifted to

Figure 8A:
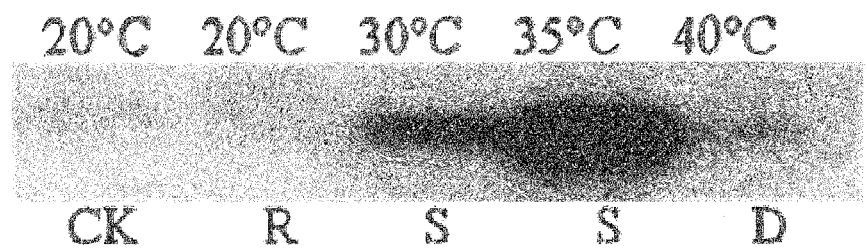
FIG. 8A is a Northern blot and phenotypic analysis of heat-stressed plants from Example 9.
Figure 8B:
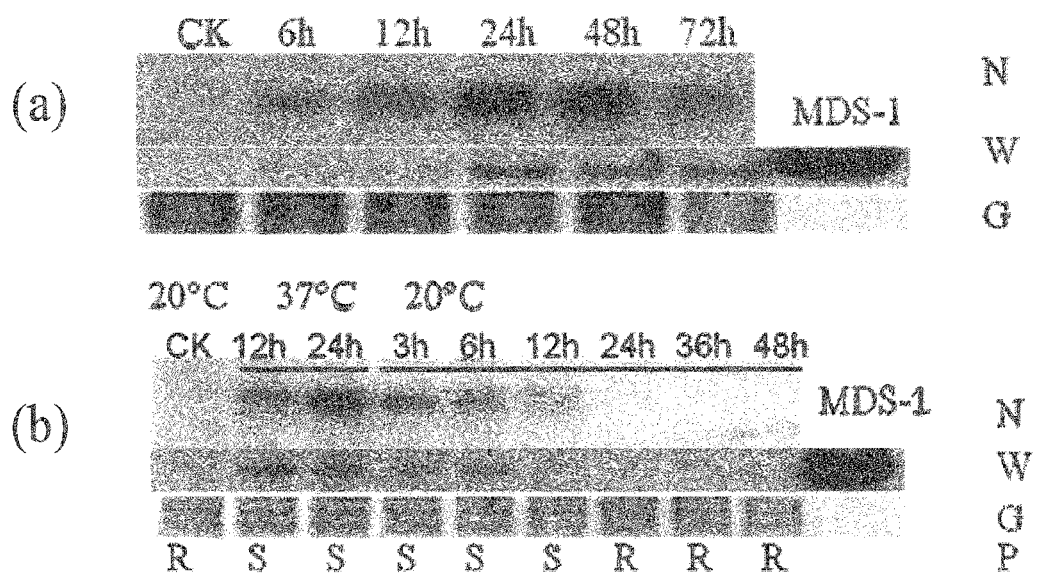
FIG. 8B shows the blotting analysis of the decay of heat-induced Mds-1 transcript and protein, and restoration of plant resistance: (a) Mds-1 induction in Molly grown at 37° C. for 6, 12, 24, 48, and 72 h, respectively; and (b) correlation between Mds-1 expression and phenotypic switches of Molly.

20° C. for recovery, FIG. 8B(b) shows the results of this test. Molly seedlings were grown at 37° C. for 12 h or 24 h, as indicated in the Figure to induce Mds-1. Some of the seedlings heated for 24 h were taken back to 20° C. for recovery for 3 h to 48 h. Resistant (R) or susceptible (S) phenotypes (P) of control, heated, and recovered plants are indicated in the figure. By infesting these plants with Hessian fly larvae at different times during recovery, a correlation between elevated Mds-1 expression and wheat susceptibility was observed.

Figure 9:
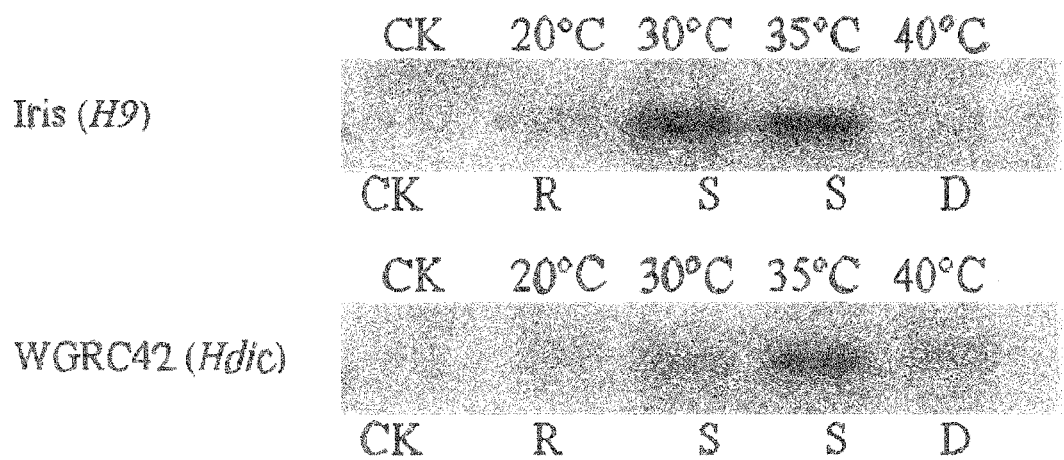
FIG. 9 shows the results from blotting analysis of the relationship of expression levels of Mds-1 and the corresponding phenotype (R or S) from Example 9.

Similar studies with wheat cultivars containing other R genes revealed the same results: elevated levels of Mds-1 transcript and protein were associated with plant susceptibility, whereas low levels of Mds-1 transcript and protein were associated with plant resistance as shown in FIG. 9. In those studies, Iris and WGRC42 seedlings were grown at 20° C. and infested with Hessian flies. One day before Hessian fly larvae started to attack plants and feeding, some of the plants were shifted to growth chambers with either 30° C., or 35° C., or 40° C. High levels of Mds-1 transcripts were detected in plants shifted to 30° C. or 35° C. through northern blot analysis. Plants shifted to 40° C. were stressed seriously and dead afterward. In association with the Mds-1 induction, plants lost resistance and became susceptible to HF attack. The phenotype of control and heat-stressed plants in response to HF attack is given underneath the blot in FIG. 9 with the following denotations: CK—uninfested control, R—resistant, S—susceptible, and D—death of both plants and Hessian fly larvae.

Example 10

Overexpression of Mds-1

Figure 10A:
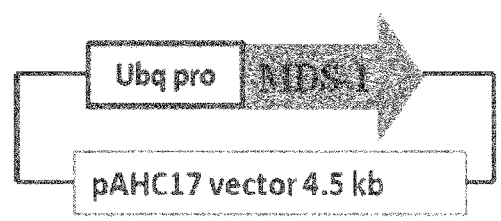
FIG. 10A is a schematic representation of the construct for over-expression of Mds-1 in wheat from Example 10.

To determine if elevated expression of Mds-1 alone in wheat with an R gene is sufficient to confer plant susceptibility, we overexpressed Mds-1 in Molly using an ubiquitin promoter (FIG. 10A). Transgenic Molly lines were obtained with a construct containing the full length Mds-1 cDNA under a maize ubiquitin promoter.

Construct for Overexpression

The overexpression construct was made according to the procedures described by Christensen et al. (1992) and Christensen and Quail (1996). To prepare the construct for Mds-1 overexpression via transgenes, the full length coding region plus a 70 bp 3'-UTR of Mds-1 was amplified by PCR using DNA polymerase AccuPrimer™ Pfx SuperMix (Invitrogen, CA, USA) with the following pair of primers: forward primer, Mds-1 1 Lc (5'-CTAGTGATCATGTCGATCGT-GCGGCGGAG (SEQ ID NO:8)), and reverse primer, Mds-1R (5'-CGCAAGAACTCGCACACACATC (SEQ ID NO:6)). The forward primer, Mds-1Lc, began at the start codon (ATG) with an added sequence that contains the BCL I restriction site "T/GATCA" plus a 4-base preceding sequence for cloning purposes. In addition, there is one BCL I restriction site "T/GATCA" within the Mds-1 gene itself located in the 3'-UTR between the stop codon and the reverse primer Mds-1R. The PCR product was digested with BCl I, and the resulting 480-bp DNA fragment was ligated into the vector pAHC17 at the unique Bam HI site (G/GATCC). Thus, the resulting overexpression construct contained the full Mds-1 coding region driven for expression by the maize ubiquitin promoter (Ubi-1), as depicted in FIG. 10A.

Figure 10B:
FIG. 10B illustrates the results from PCR detection (771 bp) for the presence of the Mds-1 construct in the transgenic wheat plants from Example 10.
Figure 10C:
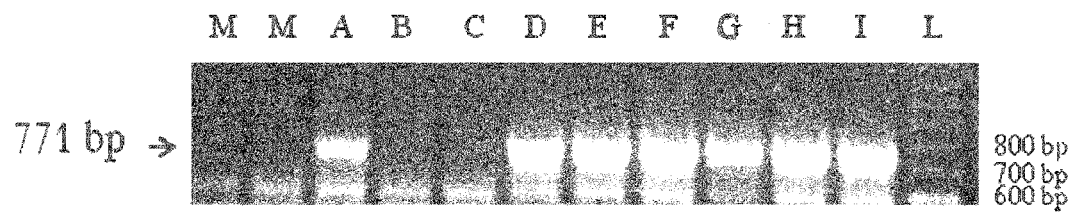
FIG. 10C illustrates additional results from PCR detection of the Mds-1 overexpression construct from Example 10.

Next, the pAHC17 Mds-1 construct and the pAHC20 vector were co-bombarded into the wheat cultivar Molly following the same procedure as described in Example 7 above for knockdown. The presence of the Mds-1 overexpression construct in the transgenic plants was confirmed by PCR using the gene specific forward primer, Mds-1F (5'-ATGTCGATCGTGCGGCGGAG (SEQ ID NO:9)), and a vector primer, ACH17-R (5'-TTCTCATGTTTGACAGCT-TATCATCG (SEQ ID NO:13)). As shown in FIGS. 10B-10C, the PCR fragment was a 771 bp sequence. In FIG. 10B, Pl indicates the plasmid DNA used as the positive control. M indicates the untransformed Molly as a negative control. T1 to T3 indicate three independent transgenes, and L indicates the DNA ladders, FIG. 10C shows the PCR detection of the Mds-1 overexpression construct in transformed Molly Plants. Samples were derived from either non-transgenic Molly (M) or independent Molly transgenes (A-I). Transgenes B and C were herbicide-positive, but did not amplify the Mds-1 overexpression construct. The other seven transgenes had PCR bands with the expected size (771 bp). As with FIG. 10B, the letter L indicates the DNA marker ladder. Genomic Southern blot analysis was also conducted to confirm the integration of the Mds-1 construct into the wheat genome performed as described in Example 3.

Results

Figure 11:
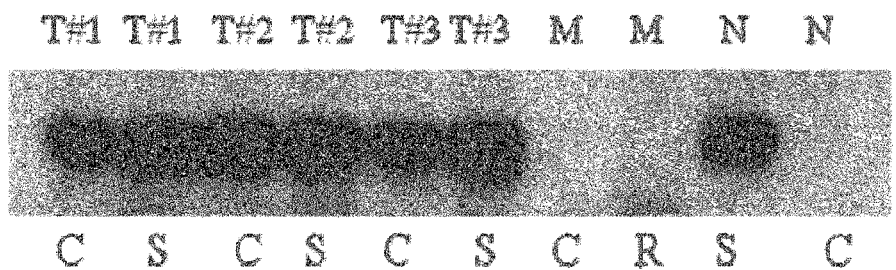
FIG. 11 is a Northern blot and phenotypic analysis of transgenes T#1, T#2, and T#3, and non-transgenic controls Molly (M) and Newton (N) from Example 10.

The plants were then infested with Hessian flies. Mds-1 transcript was analyzed via Northern blots in independent transgenes T#1, T#2, and T#3, and in non-transgenic controls Molly (M) and Newton (N, susceptible with no R gene). Plant phenotypes are given in FIG. 11. When Mds-1 was overexpressed in Molly seedlings, plants lost resistance despite the presence of H13 and instead became susceptible to Hessian fly attack. The loss of wheat resistance due to Mds-1 overexpression suggested that high levels of Mds-1 expression had a dominant effect on R gene function and was sufficient to make plants susceptible even in the present of an R gene. The results are summarized in Table 3 below.

TABLE 3

Summary of Molly transgenic plants containing the Mds-1 overexpression construct*

| Plant | Bar | GOIa | GOIb | PHF | PPM | Seeds |
|---|---|---|---|---|---|---|
| 640a, b, c, | + | NA | + | ab S | S | yes |
| 691 | + | NA | − | R | S | Disposed |
| 793 | + | NA | − | R | S | yes |
| 1111 | + | NA | + | S | S | yes |
| 1117a, b | + | NA | + | S | S | yes |
| 1490 | + | NA | + | S | S | yes |
| 1905 | − | NA | − | R | S | Disposed |
| 1984 | − | NA | − | R | S | Disposed |
| 1996 | − | NA | − | R | S | Disposed |

*The letters after a transgene number represent different tillers when the plants were infested with Hessian fly or powdery mildew.
Bar, GOIa, and GOIb represent PCR detection results of the presence of the Bar gene (herbicide resistance), inserted gene at antisense, and sense orientation, respectively, in transgenic plants using a vector primer and a gene-specific primer as described herein. The negative "−" symbol indicates no PCR amplification at all.
The positive symbol "+" represents the detection of a DNA fragment with the expected size.
NA means not applicable or not determined.
PHF represents resistant (R) or susceptible (S) phenotypes of the transgenes to Hessian fly infestation.
PPM represents resistant or susceptible phenotypes of transgenes to powdery mildew infection.
Seeds represents transgenic plants that produced seeds successfully (yes) or did not reach the seed production stage (dead).
"Disposed" represents plants were disposed before they reached the flowing stage.

Example 11

Epidermal Cell Permeability

When plants are infested with insects, increased cell permeability is often associated with cell wall alterations and is taken as an indicator for nutritive cell formation.

Since Hessian flies manipulate host plants and its survival depends on the formation of nutritive cells, we then examined if Mds-1 knockdown interferes with Hessian fly plant manipulation by examining wheat epidermal cell permeability.

Hessian fly biotype GP was used for infestations of various Molly and Bobwhite wheat cultivars. Neutral red stain (Sigma-Aldrich, St. Louis, Mo., USA) was used to determine epidermal permeability of cells as described by Kosma et al (2010). Plants were dissected 3 days after the initial Hessian fly larval attack. After peeling off the first leaf-sheath of each plant, the Hessian fly larval feeding site of the second leaf-sheath was stained with 0.1% neutral red stain for 10 min., followed by five times washing with water. Uninfested plants were dissected and stained as negative controls in the same way. After staining, plant tissues were examined under a fluorescent microscope (Zeiss Axioplan-2) and photographed with a Nikon Coolpix 4500 Digital camera.

Figure 12:
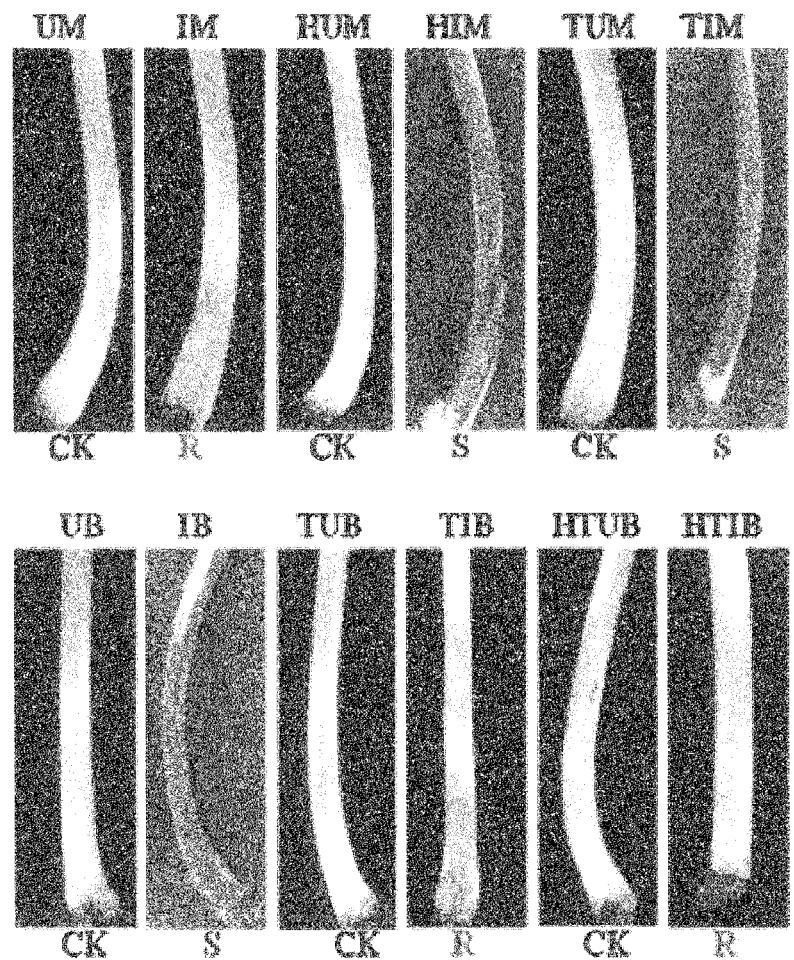
FIG. 12 shows photographs of the epidermal permeability staining results from Example 11.

The resulting images are shown in FIG. 12, with the label designations being indicated in Table 4 below.

TABLE 4

| Label | Designation |
| --- | --- |
| UM | Uninfested (control) Molly |
| IM | Infested Molly |
| HUM | Heat-stressed (37° C., 24 h), uninfested Molly |
| HIM | Heat-stressed (37° C., 24 h), infested Molly |
| TUM | Transgenic (overexpressing Mds-1), uninfested Molly |
| TIM | Transgenic (overexpressing Mds-1), infested Molly |
| UB | Uninfested (control) Bobwhite |
| IB | Infested Bobwhite |
| TUB | Transgenic (with Mds-1 knockdown), uninfested Bobwhite |
| TIB | Transgenic (with Mds-1 knockdown), infested Bobwhite |
| HTUB | Heat-stressed, transgenic (with Mds-1 knockdown), uninfested Bobwhite |
| HTIB | Heat-stressed, transgenic (with Mds-1 knockdown), infested Bobwhite |

As seen in FIG. 12, strong staining was observed with infested samples of Molly plants stressed by heat, Molly transgenes with Mds-1 overexpressed, and Bobwhite. All of the plants with strong stain were susceptible (S) to HF. No or weak staining was observed with uninfested control plants, and infested Molly seedlings under a normal temperature, and Bobwhite transgenes with Mds-1 knocked down with/without heat-stress. Infested plants with no or weak staining exhibited resistant (R) phenotypes. We found that when Mds-1 was knocked down, cell permeability was low and plants became resistant even without the existence of an R gene. However, when Mds-1 was overexpressed either through a transgene or with heat stress, cell permeability was high and plants became susceptible even in the presence of an R gene.

Figure 13:
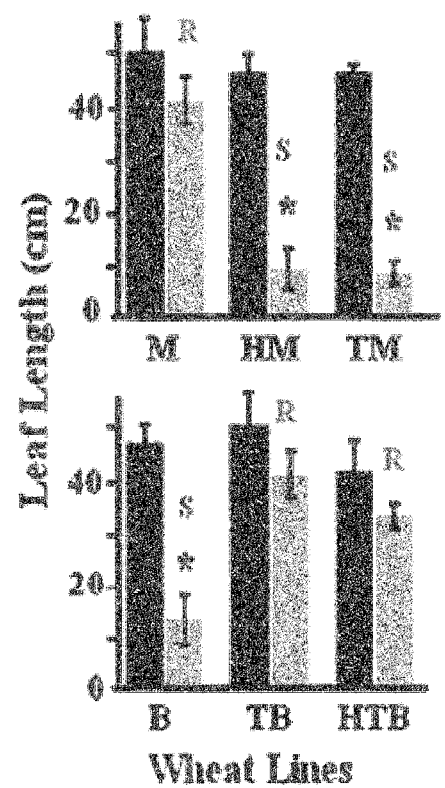
FIG. 13 provides graphs of the results from analyzing the relationship of epidermal permeability staining and wheat growth from Example 11.

Leaf lengths of the third leaf were also measured to determine effect of cell permeability on plant growth, as shown in FIG. 13. The black bars represent uninfested controls whereas gray bars represent infested plants. Designations for the graphs are as follows: M (Molly), HM (heat-stressed Molly), TM (transgenic Molly), B (Bobwhite), TB (transgenic Bobwhite), and HTB (heat-stressed, transgenic Bobwhite). Resistant (R) and susceptible (S) phenotypes of infested plants are shown above the bars. Statistically significant inhibition of wheat growth was observed only in those plants having strong epidermal permeability staining, as observed in FIG. 12.

The impact of Hessian fly infestation on the levels of transcripts of various genes were assessed. Genes studied in this Example were: (1) those involved in nutrient metabolism that are upregulated in susceptible plants, including genes of an amino transporter (BJ275567) (I), an enolase (CK208852) (II), and a methionine synthase (CN012484) (III); and (2) a group of genes involved in plant defense that are upregulated in resistant plants, including genes of a lipid transfer protein (AF334185) (IV), a family II extracellular lipase 1 (BQ171153) (V), and a class III peroxidase (CK200808) (VI). For analysis, qPCR was performed on an ABI PRISM 7000 SDS (Applied Biosystems, Foster City, Calif., USA) using iQ™ SYBR® GREEN Supermix (BIO-RAD) and the flowing program: 95° C. for 5 min., 40 cycles each consisting of 95° C. for 30 s, 55° C. for 15 s, and 72° C. for 45 s. At the end of each qPCR, a melt curve was generated to rule out the possibility of primer-dimer formation. Primers were designed based on Affymetrix™ Gene Chip EST sequences and sequences in GeneBank using the software package Beacon Designer 7. The primers are listed in Table 5, below.

TABLE 5

Primers used for qPCR

| Gene Name | GenBank # | Primer | |
| --- | --- | --- | --- |
| Amino acid transporter | BJ275567 | Forward: 5'-TCCCAATAAACGAACCCTAA | (SEQ ID NO: 14) |
| | | Reverse: 5'-TGCAAAGGACTTCTTTCATG | (SEQ ID NO: 15) |
| Enolase | CK208852 | Forward: 5'-GATTAGAAATAAAGGCACCGA | (SEQ ID NO: 16) |
| | | Reverse: 5'-GTCCGTCAAGCAAAATGT | (SEQ ID NO: 17) |
| Methionine synthase | CN012484 | Forward: 5'-TGTGATAGTGCCAGTTGA | (SEQ ID NO: 18) |
| | | Reverse: 5'-GAAGGACAGGAGTTCATCT | (SEQ ID NO: 19) |
| Lipid transfer protein | AF334185 | Forward: 5'-TGCTCTGATATGATCTCCAT | (SEQ ID NO: 20) |
| | | Reverse: 5'-ATCCTATATGATAAGCGTACATC | (SEQ ID NO: 21) |
| Family II extracellular lipase | BQ171153 | Forward: 5'-TGAACCTCTAGCCTTTACC | (SEQ ID NO: 22) |
| | | Reverse: 5'-CAATGGACGCATGAACAA | (SEQ ID NO: 23) |
| Type III peroxidase | CK200808 | Forward: 5'-GAAGCATATACTCCTACTCTTG | (SEQ ID NO: 24) |
| | | Reverse: 5'-CATGTGAGAGATCAGTTAGTT | (SEQ ID NO: 25) |

TABLE 5-continued

Primers used for qPCR

| Gene Name | GenBank # | Primer |
|---|---|---|
| Actin | AF326781 | Forward: 5'-AAATCTGGCATCACACTTTCTAC (SEQ ID NO: 26)<br>Reverse: 5'-GTCTCAAACATAATCTGGGTCATC (SEQ ID NO: 27) |

Figure 14:
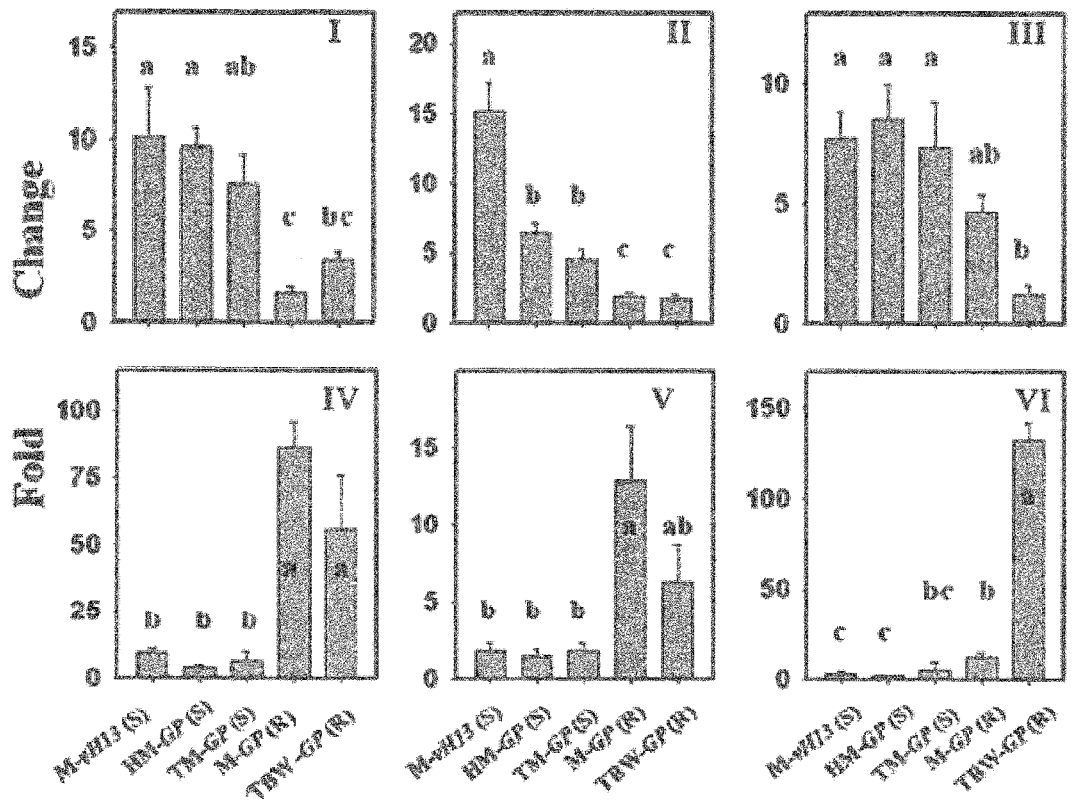
FIG. 14 provides graphs of the impact of Hessian fly infestation on the levels of transcripts of various groups of genes that are upregulated in either resistant or susceptible plants from Example 11.

For each treatment, RNA was collected from three biological replicates. Total RNA was treated with TURBO™ DNA-free (Ambion, Austin, Tex.) to remove any possible DNA contamination. First-strand cDNA was synthesized using iScript cDNA synthesis kit (BIO-RAD) with 1 μg of total RNA. The Actin gene was used as an internal reference to normalize the transcript values. Fold change was generated using the $2^{-\Delta\Delta CT}$ method. Data were subjected to ANOVA analysis and Fisher's least significant difference (LSD) multiple comparisons. Statistical analyses were performed using ProStat software (Poly Software International Inc., Pearl River, N.Y., USA). The results are shown in FIG. 14. Labels on the abscissa are shown in Table 6 below.

TABLE 6

| Labels | Designation |
|---|---|
| M-vH13 (S) | Molly (with the R gene H13) attacked by the virulent biotype vH13 (plants were susceptible to the virulent biotype). |
| HM-GP (S) | Heat-stressed Molly attacked by the avirulent biotype GP (plants became susceptible to an avirulent biotype as a result of heat-stress that induces Mds-1). |
| TM-GP (S) | Transgenic Molly attacked by the avirulent biotype GP (plants became susceptible to the avirulent biotype due to the overexpression of Mds-1 via transgene). |
| M-GP (R) | Molly attacked by the avirulent biotype GP (plants were resistant to the avirulent biotype). |
| TBW-GP (R) | Transgenic Bobwhite attacked by biotype GP (plants without a Hessian fly R gene became resistant due to Mds-1 knockdown via RNAi transgene). |

In general, Molly plants with Mds-1 overxpressed via heat-stress or transgene exhibited upregulation of genes involved in nutrient metabolism, and no significant changes in the transcript levels of genes involved in plant defense, indicating that high levels of Mds-1 expression is sufficient for avirulent Hessian fly to manipulate gene expression of host plants and make them susceptible despite the presence of an R gene. On the other hand, resistant Bobwhite from Mds-1 knockdown exhibited expression patterns more variable in comparison with resistant Molly that contains an R gene, indicating that the R gene does also play some other roles in plant defense in addition to suppress Mds-1 expression.

We claim:

1. A resistant wheat plant having increased resistance to a pest relative to a control plant, said control plant comprising a wild-type susceptibility gene, said wild-type susceptibility gene being expressed in the presence of said pest, wherein said resistant plant comprises a corresponding susceptibility gene, the expression, activity, or function of said susceptibility gene being inhibited in said resistant plant, wherein said resistant plant comprises a nucleic acid construct that inhibits expression, activity, or function of said susceptibility gene, and wherein said susceptibility gene is *Mayetiola destructor* susceptibility gene 1 (Mds-1) and encodes for a heat shock protein, wherein said pest is selected from the group consisting of galling insects, sucking insects, fungal pathogens, and combinations thereof, and wherein said susceptibility gene comprises SEQ ID NO: 2 or comprises at least 90% sequence identity with SEQ ID NO: 2, or encodes an amino acid sequence comprising SEQ ID NO: 3 or an amino acid sequence comprising at least 80% amino acid identity with SEQ ID NO: 3.

2. The resistant wheat plant of claim 1, wherein said nucleic acid construct comprises a sense sequence operably linked to its complementary antisense sequence and encoding double stranded RNA that inhibits expression, activity, or function of said susceptibility gene.

3. A method of producing a resistant wheat plant having increased resistance to a pest relative to a corresponding control plant, said control plant comprising a wild-type susceptibility gene, said wild-type susceptibility gene being expressed in the presence of said pest, said method comprising: inhibiting the expression, activity, or function of a susceptibility gene in a plant to thereby produce said resistant plant, wherein said inhibiting comprises introducing into a plant tissue, organ, part, or cell a nucleic acid construct that inhibits expression, activity, or function of said susceptibility gene, and wherein said susceptibility gene is Mds-1 and encodes for a heat shock protein, wherein said pest is selected from, the group consisting of galling insects, sucking insects, fungal pathogens, and combinations thereof,
and wherein said susceptibility gene comprises SEQ ID NO: 2 or comprises at least 90% sequence identity with SEQ ID NO: 2, or
encodes an amino acid sequence comprising SEQ ID NO: 3 or an amino acid sequence comprising at least 80% amino acid identity with SEQ ID NO: 3.

4. The method of claim 3, wherein said nucleic acid construct comprises:
a sense sequence that encodes double stranded RNA which inhibits expression, activity, or function of said susceptibility gene, or
a sense sequence operably linked to its complementary antisense sequence and encoding double stranded RNA that inhibits expression, activity, or function of said susceptibility gene.

5. The method of claim 4, wherein said sense sequence comprises SEQ ID NO: 4 or a sequence having at least 90% sequence identity with SEQ ID NO: 4.

6. The method of claim 3, wherein said pest is *Mayetiola destructor*, said wild-type susceptibility gene being expressed in the presence of *Mayetiola destructor*, wherein said inhibiting comprises:
(a) culturing immature plant embryos to form callus tissue;
(b) introducing said nucleic acid construct into said tissue to produce modified plant cells; and
(c) regenerating resistant plants from said modified plant cells, wherein the expression, activity, or function of said susceptibility gene in said resistant plants is inhibited in the presence of *Mayetiola destructor*.

7. The method of claim 6, wherein said introducing (b) comprises transforming said callus tissue by delivering a selection gene and DNA coding for an antisense Mds-1 sequence into the cells of said callus tissue, and selecting for *Mayetiola destructor* resistance by growing transformed cells on media and selecting for the selection gene, wherein the resistant plant transcribes the Mds-1 sequence to form dsRNA.

8. The method of claim 6, wherein said introducing (b) comprises transforming said callus tissue by delivering a selection gene and DNA coding for a sense Mds-1 sequence and antisense Mds-1 sequence into the cells of said callus tissue and selecting for *Mayetiola destructor* resistance by growing transformed cells on media and selecting for the selection gene, wherein the resistant plant transcribes the Mds-1 sequence to form dsRNA.

9. A seed of a resistant wheat plant according to claim 1, wherein the seed comprises the nucleic acid construct that inhibits expression, activity, or function of the Mds-1 susceptibility gene of claim 1.

10. The resistant wheat plant of claim 1, wherein said resistant plant is a transgenic wheat plant comprising a nucleotide sequence that encodes and/or is complementary to a sequence that encodes a Mds-1 polynucleotide sequence of SEQ ID NO: 4 or a Mds-1 polynucleotide sequence comprising an antisense sequence corresponding to SEQ ID NO: 4, wherein said transgenic plant has increased resistance to *Mayetiola destructor*.

11. A transgenic wheat plant having decreased expression, activity, or function of a plant susceptibility gene Mds-1, wherein said plant has stably incorporated into its genome a DNA construct, wherein said DNA construct comprises at least one nucleotide sequence selected from the group consisting of:
(a) a nucleotide sequence comprising SEQ ID NO: 4;
(b) a nucleotide sequence comprising an antisense sequence corresponding to SEQ ID NO: 4;
(c) a nucleotide sequence having at least about 90% sequence identity to SEQ ID NO: 4;
(d) a nucleotide sequence encoding an Mds-1 protein comprising SEQ ID NO: 4; and
(e) a nucleotide sequence encoding an Mds-1 protein having at least 80% amino acid identity to SEQ ID NO: 3 and retaining the functional characteristics thereof,
wherein said nucleotide sequence is operably linked to a promoter capable of regulating transcription of said sequence in said plant.

12. A method for increasing or enhancing resistance to a pest in a wheat plant wherein said pest is selected from the group consisting of galling insects, sucking insects, fungal pathogens, and combinations thereof, said method comprising:
providing a first parent plant, said first parent plant being a resistant wheat plant according to claim 1 and having increased resistance to a pest relative to a control plant;
crossing said first parent plant with a second parent plant to produce progeny plants; and
selecting for progeny plants having the nucleic acid construct that inhibits expression, activity, or function of said susceptibility gene of claim 1, said progeny plants having increased or enhanced resistance to said pest.

* * * * *

SEQUENCE LISTING

<160> NUMBER OF SEQ ID NOS: 33

<210> SEQ ID NO 1
<211> LENGTH: 801
<212> TYPE: DNA
<213> ORGANISM: Triticum aestivum

<400> SEQUENCE: 1

```
aagcagtggt atcaacgcag agtacgcggg aagccagtgt caaccaaaag tagacagcat      60
cctcacctgc gacccaatcc agaacagatt ttttccccga gctagaaacc aaagtaacac     120
cgacgatgtc gatcgtgcgg cggagcagcg tgttcgaccc cttcgccgac ctctgggctg     180 acctttcga caccttccgc tccatcatcc cggcgatctc aggcggcaac agcgagacgg     240
ccgcgttcgc caatgctcgc atggactgga aggagacccc cgaggcgcac gtcttcaagg     300
ccgacctccc cggcgtgaag aaggaggagg tcaaggtgga ggtggaggac ggcaacgtgc     360
tcgtcgtcag cggcgagcgc acaaaggaga aggaggacaa gaacgacaag tggcaccgcg     420
tggagcgcag cagcggcaag ttcgtcaggc ggttccgcct ccccgaggac gccaaggtgg     480
aggaggtgaa ggccgggctg gagaacggtg tgctcaccgt caccgtgccc aaggcccagg     540
tcaagaagcc cgaggtgaag gccatccaga tctccggctg agtggacgcg tctcggcgta     600
tgatcatcag ggatggagcc agtttggttg atgtgtgtgc gagttcttgc gagtctgatg     660
```

```
agacatctct gtattgtgtt tctttcccca gtgttttctg tacttgtgta atcggctaat    720
cgccaacaga ttcggcgatg aataaatgag aaataaattg ttctgatttt gggtgcaaaa    780
aaaaaaaaaa aaaaaaaaaa a                                              801
```

<210> SEQ ID NO 2
<211> LENGTH: 456
<212> TYPE: DNA
<213> ORGANISM: Triticum aestivum

<400> SEQUENCE: 2

```
atgtcgatcg tgcggcggag cagcgtgttc gaccccttcg ccgacctctg ggctgaccct     60
ttcgacacct tccgctccat catcccggcg atctcaggcg gcaacagcga gacggccgcg    120
ttcgccaatg ctcgcatgga ctggaaggag accccgaggg cgcacgtctt caaggccgac    180
ctccccggcg tgaagaagga ggaggtcaag gtggaggtgg aggacggcaa cgtgctcgtc    240
gtcagcggcg agcgcacaaa ggagaaggag gacaagaacg acaagtggca ccgcgtggag    300
cgcagcagcg gcaagttcgt caggcggttc cgcctccccg aggacgccaa ggtggaggag    360
gtgaaggccg gcctggagaa cggtgtgctc accgtcaccg tgcccaaggc ccaggtcaag    420
aagcccgagg tgaaggccat ccagatctcc ggctga                              456
```

<210> SEQ ID NO 3
<211> LENGTH: 151
<212> TYPE: PRT
<213> ORGANISM: Triticum aestivum

<400> SEQUENCE: 3

```
Met Ser Ile Val Arg Arg Ser Ser Val Phe Asp Pro Phe Ala Asp Leu
1               5                   10                  15

Trp Ala Asp Pro Phe Asp Thr Phe Arg Ser Ile Ile Pro Ala Ile Ser
            20                  25                  30

Gly Gly Asn Ser Glu Thr Ala Ala Phe Ala Asn Ala Arg Met Asp Trp
        35                  40                  45

Lys Glu Thr Pro Glu Ala His Val Phe Lys Ala Asp Leu Pro Gly Val
    50                  55                  60

Lys Lys Glu Glu Val Lys Val Glu Val Glu Asp Gly Asn Val Leu Val
65                  70                  75                  80

Val Ser Gly Glu Arg Thr Lys Glu Lys Glu Asp Lys Asn Asp Lys Trp
                85                  90                  95

His Arg Val Glu Arg Ser Ser Gly Lys Phe Val Arg Arg Phe Arg Leu
            100                 105                 110

Pro Glu Asp Ala Lys Val Glu Glu Val Lys Ala Gly Leu Glu Asn Gly
        115                 120                 125

Val Leu Thr Val Thr Val Pro Lys Ala Gln Val Lys Lys Pro Glu Val
    130                 135                 140

Lys Ala Ile Gln Ile Ser Gly
145                 150
```

<210> SEQ ID NO 4
<211> LENGTH: 338
<212> TYPE: DNA
<213> ORGANISM: Triticum aestivum

<400> SEQUENCE: 4

```
cgtgaagaag gaggaggtca aggtggaggt ggaggacggc aacgtgctcg tcgtcagcgg     60
```

```
cgagcgcaca aaggagaagg aggacaagaa cgacaagtgg caccgcgtgg agcgcagcag      120
cggcaagttc gtcaggcggt tccgcctccc cgaggacgcc aaggtggagg aggtgaaggc      180
cgggctggag aacggtgtgc tcaccgtcac cgtgcccaag gcccaggtca agaagcccga      240
ggtgaaggcc atccagatct ccggctgagt ggacgcgtct cggcgtatga tcatcaggga      300
tggagccagt ttggttgatg tgtgtgcgag ttcttgcg                              338
```

```
<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
cgtgaagaag gaggaggtca ag                                               22

<210> SEQ ID NO 6
<211> LENGTH: 22
<212> TYPE: DNA
<213> ORGANISM: Artificial Sequence
<220> FEATURE:
<223> OTHER INFORMATION: PCR Primer

<400> SEQUENCE: 6
cgcaagaact cgcacacaca tc                                               22

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
acctgcgacc caatccagaa c                                                21

<210> SEQ ID NO 8
<211> LENGTH: 29
<212> TYPE: DNA
<213> ORGANISM: Artificial Sequence
<220> FEATURE:
<223> OTHER INFORMATION: PCR Primer

<400> SEQUENCE: 8
ctagtgatca tgtcgatcgt gcggcggag                                        29

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
atgtcgatcg tgcggcggag                                                  20

<210> SEQ ID NO 10
<211> LENGTH: 23
<212> TYPE: DNA
<213> ORGANISM: Artificial Sequence
<220> FEATURE:
<223> OTHER INFORMATION: PCR Primer

<400> SEQUENCE: 10
```
aagcagtggt atcaacgcag agt                                    23

<210> SEQ ID NO 11
<211> LENGTH: 19
<212> TYPE: DNA
<213> ORGANISM: Artificial Sequence
<220> FEATURE:
<223> OTHER INFORMATION: PCR Primer

<400> SEQUENCE: 11
cacgtagtcc gcatcttca                                         19

<210> SEQ ID NO 12
<211> LENGTH: 24
<212> TYPE: DNA
<213> ORGANISM: Artificial Sequence
<220> FEATURE:
<223> OTHER INFORMATION: PCR Primer

<400> SEQUENCE: 12
gtggagtgaa gagtatcagt gtgc                                   24

<210> SEQ ID NO 13
<211> LENGTH: 26
<212> TYPE: DNA
<213> ORGANISM: Artificial Sequence
<220> FEATURE:
<223> OTHER INFORMATION: PCR Primer

<400> SEQUENCE: 13
ttctcatgtt tgacagctta tcatcg                                 26

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
tcccaataaa cgaaccctaa                                        20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
tgcaaaggac ttctttcatg                                        20

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
gattagaaat aaaggcaccg a                                      21

<210> SEQ ID NO 17
<211> LENGTH: 18
<212> TYPE: DNA

```
<213> ORGANISM: Artificial Sequence
<220> FEATURE:
<223> OTHER INFORMATION: PCR Primer

<400> SEQUENCE: 17
gtccgtcaag caaaatgt                                                 18

<210> SEQ ID NO 18
<211> LENGTH: 18
<212> TYPE: DNA
<213> ORGANISM: Artificial Sequence
<220> FEATURE:
<223> OTHER INFORMATION: PCR Primer

<400> SEQUENCE: 18
tgtgatagtg ccagttga                                                 18

<210> SEQ ID NO 19
<211> LENGTH: 19
<212> TYPE: DNA
<213> ORGANISM: Artificial Sequence
<220> FEATURE:
<223> OTHER INFORMATION: PCR Primer

<400> SEQUENCE: 19
gaaggacagg agttcatct                                                19

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
tgctctgata tgatctccat                                               20

<210> SEQ ID NO 21
<211> LENGTH: 23
<212> TYPE: DNA
<213> ORGANISM: Artificial Sequence
<220> FEATURE:
<223> OTHER INFORMATION: PCR Primer

<400> SEQUENCE: 21
atcctatatg ataagcgtac atc                                           23

<210> SEQ ID NO 22
<211> LENGTH: 19
<212> TYPE: DNA
<213> ORGANISM: Artificial Sequence
<220> FEATURE:
<223> OTHER INFORMATION: PCR Primer

<400> SEQUENCE: 22
tgaacctcta gcctttacc                                                19

<210> SEQ ID NO 23
<211> LENGTH: 18
<212> TYPE: DNA
<213> ORGANISM: Artificial Sequence
<220> FEATURE:
<223> OTHER INFORMATION: PCR Primer

<400> SEQUENCE: 23
caatggacgc atgaacaa                                                 18
```

<210> SEQ ID NO 24
<211> LENGTH: 22
<212> TYPE: DNA
<213> ORGANISM: Artificial Sequence
<220> FEATURE:
<223> OTHER INFORMATION: PCR Primer

<400> SEQUENCE: 24
gaagcatata ctcctactct tg                                              22

<210> SEQ ID NO 25
<211> LENGTH: 21
<212> TYPE: DNA
<213> ORGANISM: Artificial Sequence
<220> FEATURE:
<223> OTHER INFORMATION: PCR Primer

<400> SEQUENCE: 25
catgtgagag atcagttagt t                                               21

<210> SEQ ID NO 26
<211> LENGTH: 23
<212> TYPE: DNA
<213> ORGANISM: Artificial Sequence
<220> FEATURE:
<223> OTHER INFORMATION: PCR Primer

<400> SEQUENCE: 26
aaatctggca tcacactttc tac                                             23

<210> SEQ ID NO 27
<211> LENGTH: 24
<212> TYPE: DNA
<213> ORGANISM: Artificial Sequence
<220> FEATURE:
<223> OTHER INFORMATION: PCR Primer

<400> SEQUENCE: 27
gtctcaaaca taatctgggt catc                                            24

<210> SEQ ID NO 28
<211> LENGTH: 26
<212> TYPE: DNA
<213> ORGANISM: Artificial Sequence
<220> FEATURE:
<223> OTHER INFORMATION: PCR Primer

<400> SEQUENCE: 28
cctgccttca tacgctattt atttgc                                          26

<210> SEQ ID NO 29
<211> LENGTH: 25
<212> TYPE: DNA
<213> ORGANISM: Artificial Sequence
<220> FEATURE:
<223> OTHER INFORMATION: PCR Primer

<400> SEQUENCE: 29
cttcagcagg tgggtgtaga gcgtg                                           25

<210> SEQ ID NO 30
<211> LENGTH: 151
<212> TYPE: PRT
<213> ORGANISM: Triticum aestivum

```
<400> SEQUENCE: 30

Met Ser Ile Val Arg Arg Ser Asn Val Phe Asp Pro Phe Ala Asp Leu
1               5                   10                  15

Trp Ala Asp Pro Phe Asp Thr Phe Arg Ser Ile Val Pro Ala Ile Ser
            20                  25                  30

Gly Gly Gly Ser Glu Thr Ala Ala Phe Ala Asn Ala Arg Met Asp Trp
        35                  40                  45

Lys Glu Thr Pro Glu Ala His Val Phe Lys Ala Asp Leu Pro Gly Val
50                  55                  60

Lys Lys Glu Glu Val Lys Val Glu Val Glu Asp Gly Asn Val Leu Val
65                  70                  75                  80

Val Ser Gly Glu Arg Thr Lys Glu Lys Glu Asp Lys Asn Asp Lys Trp
                85                  90                  95

His Arg Val Glu Arg Ser Ser Gly Lys Phe Val Arg Arg Phe Arg Leu
            100                 105                 110

Leu Glu Asp Ala Lys Val Glu Glu Val Lys Ala Gly Leu Glu Asn Gly
        115                 120                 125

Val Leu Thr Val Thr Val Pro Lys Ala Glu Val Lys Lys Pro Glu Val
    130                 135                 140

Lys Ala Ile Gln Ile Ser Gly
145                 150

<210> SEQ ID NO 31
<211> LENGTH: 150
<212> TYPE: PRT
<213> ORGANISM: Oryza sativa Japonica

<400> SEQUENCE: 31

Met Ser Leu Val Arg Arg Ser Asn Val Phe Asp Pro Phe Ser Leu Asp
1               5                   10                  15

Leu Trp Asp Pro Phe Asp Ser Val Phe Arg Ser Val Val Pro Ala Thr
            20                  25                  30

Ser Asp Asn Asp Thr Ala Ala Phe Ala Asn Ala Arg Ile Asp Trp Lys
        35                  40                  45

Glu Thr Pro Glu Ser His Val Phe Lys Ala Asp Leu Pro Gly Val Lys
50                  55                  60

Lys Glu Glu Val Lys Val Glu Val Glu Gly Asn Val Leu Val Ile
65                  70                  75                  80

Ser Gly Gln Arg Ser Lys Glu Lys Glu Asp Lys Asn Asp Lys Trp His
                85                  90                  95

Arg Val Glu Arg Ser Ser Gly Gln Phe Met Arg Arg Phe Arg Leu Pro
            100                 105                 110

Glu Asn Ala Lys Val Asp Gln Val Lys Ala Gly Leu Glu Asn Gly Val
        115                 120                 125

Leu Thr Val Thr Val Pro Lys Ala Glu Val Lys Lys Pro Glu Val Lys
    130                 135                 140

Ala Ile Glu Ile Ser Gly
145                 150

<210> SEQ ID NO 32
<211> LENGTH: 157
<212> TYPE: PRT
<213> ORGANISM: Arabidopsis thaliana

<400> SEQUENCE: 32

Met Ser Leu Ile Pro Ser Ile Phe Gly Gly Arg Arg Thr Asn Val Phe
```

-continued

```
1               5                   10                  15
Asp Pro Phe Ser Leu Asp Val Phe Asp Pro Phe Glu Gly Phe Leu Thr
                20                  25                  30

Pro Ser Gly Leu Ala Asn Ala Pro Ala Met Asp Val Ala Ala Phe Thr
                35                  40                  45

Asn Ala Lys Val Asp Trp Arg Glu Thr Pro Glu Ala His Val Phe Lys
        50                  55                  60

Ala Asp Leu Pro Gly Leu Arg Lys Glu Val Lys Val Glu Val Glu
65                  70                  75                  80

Asp Gly Asn Ile Leu Gln Ile Ser Gly Glu Arg Ser Asn Glu Asn Glu
                85                  90                  95

Glu Lys Asn Asp Lys Trp His Arg Val Glu Arg Ser Ser Gly Lys Phe
                100                 105                 110

Thr Arg Arg Phe Arg Leu Pro Glu Asn Ala Lys Met Glu Glu Ile Lys
            115                 120                 125

Ala Ser Met Glu Asn Gly Val Leu Ser Val Thr Val Pro Lys Val Pro
        130                 135                 140

Glu Lys Lys Pro Glu Val Lys Ser Ile Asp Ile Ser Gly
145                 150                 155
```

<210> SEQ ID NO 33
<211> LENGTH: 154
<212> TYPE: PRT
<213> ORGANISM: Solanum lycopersicum

<400> SEQUENCE: 33

```
Met Ser Leu Ile Pro Arg Ile Phe Gly Asp Arg Arg Ser Ser Ser Met
1               5                   10                  15

Phe Asp Pro Phe Ser Ile Asp Val Phe Asp Pro Phe Arg Glu Leu Gly
                20                  25                  30

Phe Pro Ser Thr Asn Ser Gly Glu Ser Ser Ala Phe Ala Asn Thr Arg
            35                  40                  45

Ile Asp Trp Lys Glu Thr Pro Glu Ala His Val Phe Lys Val Asp Leu
        50                  55                  60

Pro Gly Leu Lys Lys Glu Glu Val Lys Val Glu Val Glu Glu Asp Arg
65                  70                  75                  80

Val Leu Gln Ile Ser Gly Glu Arg Asn Val Glu Lys Glu Asp Lys Asn
                85                  90                  95

Asp Lys Trp His Arg Met Glu Arg Ser Ser Gly Lys Phe Met Arg Arg
                100                 105                 110

Phe Arg Leu Pro Glu Asn Ala Lys Met Asp Gln Val Lys Ala Ser Met
            115                 120                 125

Glu Asn Gly Val Leu Thr Val Thr Val Pro Lys Glu Glu Val Lys Lys
        130                 135                 140

Pro Glu Val Lys Ser Ile Glu Ile Ser Gly
145                 150
```